(12) United States Patent
Carron et al.

(10) Patent No.: US 6,770,488 B1
(45) Date of Patent: Aug. 3, 2004

(54) PRACTICAL METHOD AND APPARATUS FOR ANALYTE DETECTION WITH COLLOIDAL PARTICLES

(75) Inventors: Keith T. Carron, Centennial, WY (US); Robert C. Corcoran, Laramie, WY (US); Roberta Ann Sulk, Laramie, WY (US)

(73) Assignee: The University of Wyoming, Laramie, WY (US)

( * ) Notice: Subject to any disclaimer, the term of this patent is extended or adjusted under 35 U.S.C. 154(b) by 0 days.

(21) Appl. No.: 09/527,226

(22) Filed: Mar. 16, 2000

Related U.S. Application Data
(60) Provisional application No. 60/125,368, filed on Mar. 19, 1999.

(51) Int. Cl.[7] ............................................. G01N 33/553
(52) U.S. Cl. ........................ 436/525; 435/7.1; 435/968; 435/973; 436/164; 436/166; 436/172; 436/518; 436/523; 436/524; 436/536; 436/539; 436/540; 436/541; 436/805; 356/301; 356/317; 356/318; 356/337
(58) Field of Search ......................... 435/7.1, 968, 973; 436/164, 166, 172, 518, 523, 524, 525, 536, 539, 540, 541, 805; 356/301, 317, 318, 337

(56) References Cited

U.S. PATENT DOCUMENTS

| | | | |
|---|---|---|---|
| 3,062,612 A | 11/1962 | LeBoucher | |
| RE30,627 E | 5/1981 | Bagshawe et al. | 23/230 R |
| 4,284,553 A | 8/1981 | Brown et al. | 260/112 R |
| 4,674,878 A | 6/1987 | Vo-Dinh | 356/301 |
| 4,781,458 A | 11/1988 | Angel et al. | 356/301 |
| 4,802,761 A | 2/1989 | Bowen et al. | 356/301 |
| 4,844,613 A | 7/1989 | Batchelder et al. | 356/318 |
| 4,857,273 A | 8/1989 | Stewart | 422/68 |
| 4,877,747 A | 10/1989 | Stewart | 436/525 |
| 4,939,264 A | 7/1990 | Heiman et al. | 436/537 |
| 5,017,007 A | 5/1991 | Milne et al. | 356/301 |
| 5,023,053 A | 6/1991 | Finlan | 422/82.05 |
| 5,132,097 A | 7/1992 | Van Deusen et al. | 422/82.09 |
| 5,144,030 A | 9/1992 | Wang et al. | 546/89 |
| 5,255,067 A | 10/1993 | Carrabba et al. | 356/301 |
| 5,262,333 A | 11/1993 | Heiman et al. | 436/537 |
| 5,266,498 A | 11/1993 | Tacha et al. | 436/525 |
| 5,294,402 A | 3/1994 | Schrepp et al. | 422/57 |
| 5,327,211 A | 7/1994 | Carron et al. | 356/301 |
| 5,376,556 A | 12/1994 | Tarcha et al. | 436/525 |
| 5,400,136 A | 3/1995 | Vo-Dinh | 356/301 |
| 5,496,700 A | 3/1996 | Ligler et al. | 435/7.1 |
| 5,567,628 A | 10/1996 | Tarcha et al. | 436/525 |
| 5,576,216 A | 11/1996 | Patchornik | 436/86 |
| 5,607,643 A | 3/1997 | Xiaoming et al. | 422/82.05 |
| 5,618,926 A | 4/1997 | Salamone et al. | 530/403 |
| 5,693,152 A | 12/1997 | Carron | 148/271 |
| 5,834,224 A | 11/1998 | Ruger et al. | 435/14 |

OTHER PUBLICATIONS

Albert, B., et al., *Molecular Biology of THE CELL, Second Edition;* pp 125–126 and pp 167–168, (1989).

Boyer, J. H.; Canter, F.C., *Alkyl and Aryl Azides,* Chemical Reviews, 54, pp 1–20, (1954).

*Complete Low–Cost Raman Systems, The New Solution™ Series,* 7 pages.

(List continued on next page.)

*Primary Examiner*—Christopher L. Chin
(74) *Attorney, Agent, or Firm*—Santangelo Law Offices, P.C.

(57) ABSTRACT

A colloidal system for detection of a variety of analytes involves techniques which permit reconstitution of a desiccated substance such as for surface enhanced Raman spectroscopic analysis and multiple sensors at once, each having different spectra through the use of markers or the like. Competitive assay techniques and a variety of substances are explained to permit a practical an versatile system which can also be used for immunological assays and can include antibodies tagged to provide spectroscopic indicia.

66 Claims, 9 Drawing Sheets

OTHER PUBLICATIONS

Dou, X., et al, *Enzyme Immunoassay Utilizing Surface–Enhanced Raman Scattering of the Enzyme Reaction Product,* Anal. Chem., vol. 69, pp 1492–1495, (1997).

E. Roth and W. Kiefer, 1994 Society for Applied Spectroscopy, *Surface–Enhanced Raman Spectroscopy as a Detection Method in Gas Chromatraphgy,* pp 1193–1195.

G.J. Rosasco and E.S. Etz, *The Raman Microprobe: A New Analytical Tool,* Research/Development, Jun. 1977, total of 17 pages.

Hegarty, A. F. in *The Chemistry of Diazonium and Diazo Groups,* part 2, S. Patai, ed.: John Wiley and Sons: New York, 1978, pp. 511–591.

Ken Mullen and Keith Carron, *Absorption of Chlorinated Ethylenes at 1–Octadecanethiol–Modified Silver Surfaces,* 1994 American Chemical Society, pp 478–483.

Lewis, E. S.; Suhr, H. *Untersuchungen über die Reaktion von Diazonium salzen mit Sulfit,* Chemische Berichte, 92, pp 3031–3043, (1959).

Machacek, V.; Machackova, O.; Sterba, V., *Kinetics and Mechanism of Diazo Coupling. XV. Coupling Kinetics of Substituted Benzenediazonium Salts with Acetone,* Collection of Czech Chemical Communications, 35, pp 2954–2964, (1970).

Machacek, V.; Machackova, O.; Sterba, V., *Kinetics and Mechanism of Diazo Coupling. XX. Coupling Kinetics of Substituted Benzenediazoniumlons with Substituted—Methylglyoxal Phenylhydrazones,* Collection of Czech Chemical Communications, ibid., 36, 3187–3196, (1971).

Mullen, Ken I.; Carron, Keith T., *Surface–Enhanced Raman Spectroscopy with Abrasively Modified Fiber Optic Probes,* Analytical Chemistry, vol. 63, No. 19, Oct. 1, 1991, 63, pp 2196–2199, (1991).

Putter, R.,*Beitrag zum Mechanismus der Azokupplung,* Angewandte Chemie, 63, 188–192, (1951).

Ritchie, C. D.; Saltiel, J. D.; Lewis, E.S., *The Reaction of Diazonium Salts with Nucleophiles. VIII. The Formation of Diazosulfones and the Application of Linear Free Energy Equations to Diazonium Salt Reactions,* Journal of the American Chemical Society, 83, 4601–4605, (1961).

Ritchie, C. D.; Wright, D. J., *Cation–Anion Combination Reactions. IV. Reactions of Aryldiazonium Ions with Hydrooxide and Cyanide Ions in Aqueous Solution,* Journal of the American Chemical Society, 93, 6574–6577, (1971).

Rohr, T. E., et al, *Immunoassay Employing Surface–Enhanced Raman Spectroscopy,* Analytical Biochemistry, vol. 182, pp 388–398, (1989).

S. E. Krahler, *p–Quinone Imine Dyes,* The Chemistry of Synthetic Dyes and Pigments, H. A. Lubs, ed.: Reinhold Publishing, New York, 1955: Chapter 5, pp. 263–266.

Zollinger, H., *Azo Coupling Reactions,* Color Chemistry, VCH Publishers, New York (1991), chapter 7.3, pp 117–127.

Ngeh–Ngwainbi, Foley, J., Kuan, P. H., Guilbault, G. G.; "Parathion Antibodies on Piezoelectric Crystals", J. Am. Chem. Soc., 1986, 108, 18, 5444–5447.

E. C. Hahn and G. G. Guilbault, "Piezoelectric Crystal Detectors and Their Applications", Ph.D. Thesis, University of New Orleans, LA, 1988, total of eight pages.

Suleiman, A. A., Guilbault, G. G.; "Recent Developments in Piezoelectric Immunosensors", Analyst, 1994, 119, 2279–2282.

Suleiman, A. A., Guilbault, G. G.; "Piezoelectric (PZ) Immunosensors and Their Applications", Analytical Letters, 1991, 24, 1283–1291.

Attili, B. S. Suleman, A. A.; "A Piezoelectric Immunosensor for the Detection of Cocaine", Microchemical Journal, 54, 1996, 174–179.

Rouhi, A.; "LAND MINES: Horrors Begging for Solutions", C&EN, Mar. 10, 1997, pp 14–22.

Katerkamp, A., Bolsmann, P., Niggemann, M., Pellmann, M., Cammann, K.; "Micro–Chemical Sensors Based On Fiber–Optic Excitation of Surface Plasmons", Mikrochim. Acta., 1995, 119, 63–72.

Ehler, T. T., Noe, L. J.; "Surface Plasmon Studies of Thin Silver/Gold Bimetallic Films", Langmuir, 1995, 11, 4177–4179, John M. Bowen, Lewis J. Noe, B. Patrick Sullivan.

Ehler, T. T., Malmberg, N., Noe, L. J.; "Characterization of Self–Assembled Alkanethiol Monolayers on Silver and Gold Using Surface Plasmon Spectroscopy", J. Phys. Chem., 1997, 101, 1268–1272.

Whelan, J. P., Kusterbeck, A. W., Wemhoff, G. A. Bredehorst, R., Ligler, F. S.; "Continuous–Flow Immunosensor for Detection of Explosives", Anal. Chem. 1993, 65, 3561–3565.

Scott Paulson, Kevin Morris and B. Patrick Sullivan; *A General Preparative Route to Self–assembled Monolayer Surfaces of Polypyridine Ligands and their Metal Complexes,* Department of Chemistry, University of Wyoming, Laramie, WY 82071–3838, USA, pp. 1615–1617.

Ligler, Frances S.; Anderson, George P.; Davidson, Peggy T.; Foch, J. Richard J.; Ives, Jeffrey T.; King, Keeley D.; Page, Greg; Stenger, David A.; Whelan, James P.; "Remote Sensing Using an Airborne Biosensor," Environmental Science & Technology; Aug. 15, 1998 v 32 n 16; p.: 2461, American Chemical Society.

Application for "Method and Apparatus for Detection of a Controlled Substance", filed Jun. 24, 1998, S/N PCT/US98/12974.

J. B. Heyns et al., "SERS Study of the Interaction of Alkali Metal Ions with Thiol–Derivatized Dibenzo–18–Crown–6", Analytical Chemistry May 1994, vol. 66, No. 9, pp. 1572–1574.

S. M. Angel et al., "Development of a Drug Assay Using Surface–Enhanced Raman Spectroscopy", SPIE 1990, vol. 1201, pp. 469–473.

R. J. Lacey, "Some Advanced in the Use of Raman Spectroscopy in Security Screening Applications", IEE Conference Publication, Apr. 1997, vol. 437, pp. 10–12.

P. R. Carey et al., "Resonance Raman Labels: A Submolecular Probe for Interactions in Biochemical and Biological Systems", Accounts of Chemical Research 1978, vol. 11, pp. 122–128.

E. L. Torres et al., "Trace Determination of Nitrogen–Containing Drugs by Surface Enhanced Raman Scattering Spectroscopy on Silver Colloids", Analytical Chemistry, Jul. 1987, vol. 59, No. 13, pp. 1626–1632.

K. I. Mullen et al., "Trace Detection of Ionic Species with Surface Enhanced Raman Spectroscopy", Spectroscopy, Jun. 1992, vol. 7, No. 5, pp. 24–31.

L. M. Cabalin et al., "Surface–Enhanced Raman Spectrometry for Detection in Liquid Chromoatography Using a Windowless Flow Cell", Talanta 1993, vol. 40, No. 11, pp. 1741–1747.

J. M. E. Storey et al., "Applications of Surface–Enhanced Raman Scattering (SERS) to Chemical Detection", Spectroscopy, Mar./Apr. 1995, vol. 10, No. 3, pp. 20–25.

E. A. Wachter et al., "Hybrid Substrate for Real–Time SERS–Based Chemical Sensors", Applied Spectroscopy, 1995, vol. 49, No. 2, pp. 193–199.

O. Zaborsky, "Immobilized Enzymes", 1973, pp. 5–48.

R. A. Messing et al., "Covalent Coupling of Alkaline Bacillus Subtilis Protease to Controlled–Pore Silica with New Simplified Coupling Technique", Chemical Abstracts, vol. 82, Mar. 3, 1975, abstract 53464d (Mol. Cell. Biochem. 1974, vol. 4, No. 3, pp. 217–220).

N. Yu. Abramov et al., "Synthesis and Spectral Luminescent Characteristics of Acylhydrazones Immobilized on the Surface of Carboxymethyl Cellose and Aerosil", Journal of Analytical Chemistry 1994, vol. 40, No. 7, pp. 636–639.

Y. C. Liu et al., Reactions of Organic Monolayers on Carbon Surfaces Observed with Unenhanced Raman Spectroscopy, Journal of the American Chemical Society, 1995, vol. 117, No. 45, pp. 11254–11259.

B. E. Baker et al., "Solution–Based Assembly of Metal Surfaces by Combinatorial Methods", Journal of the American Chemical Society , 1996, vol. 118, No. 36, pp. 8821–8722.

Y. C. Liu et al., "Raman Spectroscopic Determination of the Structure and Orientation of Organic Monolayers Chemisorbed on Carbon Electrode Surfaces", Analytical Chemistry, Jun. 1, 1997, vol. 69, No. 11, pp. 2091–2097.

W.H. Reusch "An Introduction to Organic Chemistry" 1997, Holden–Day, Inc., San Francisco, California, pp. 338–339.

T.Y. Li et al, Arch. Biochem. Biophys. 1979, 197, 477–486.

J. D. Andrade et al, SPIE, 718, 280–285.

M. Tsen et al, Anal. Chim. Acta 1995, 307, 333–340.

W. B. Caldwell et al, J. Am. Chem. Soc. 1995, 117, 6071–6082.

K. L. Morse et al, Life Sci. 1005, 23/24, 1957–1962.

R. de la Torre et al, J. Anai, Toxicol. 1996, 20, 165–170.

P. C. White et al, Analyst 1996, 121, 835–838.

K. Aoki et al, Jpn. J. Toxicol. Environ. Health 1997, 43, 285–292.

C. Gojon et al, Sens. Actuators B 1997, 38–39, 154–162.

V. Matejec et al, Sens. Actuators B 1997, 38–39, 438–442.

PRACTICAL METHOD AND APPARATUS FOR ANALYTE DETECTION WITH COLLOIDAL PARTICLES

This application claims the benefit of United States Provisional Patent Application No. 60/125,368, filed Mar. 19, 1999, hereby incorporated by reference.

BACKGROUND OF THE INVENTION

Generally, this invention relates to a method of determining the concentration of an analyte in a mixture using a spectrographic method of analysis and unique methods of spectral analysis. Specifically, the invention covers the use of Raman spectroscopy, desiccated metal particles, molecular specific coatings, sample containers, and multivariate analysis to determine the concentration of an analyte.

One of the first examples of the importance of chemical analysis in the chemical industry comes from Pliny the Elder (AD 23-79). Pliny the Elder was concerned about contamination of copper sulfate with iron sulfate. Copper sulfate was the principle ore for making copper and bronze. The purity of the copper ore ultimately determined the purity of the copper or bronze. Pliny the Elder found that the extract of gallnuts turned black in the presence of iron sulfate. This simple visual test was the first example of what today is known as Analytical Chemistry.

Since this early work in metallurgical process control the field of analytical chemistry has expanded greatly. The methods of analysis encompass 4 categories. The oldest, represented by Pliny the Elder's work, is wet chemistry. This method involves mixing chemicals together to observe a quantitative change. The other three categories are more modern and represent an improvement in sensitivity, measurement time, and selectivity over wet chemical methods. These methods are: spectroscopy, chromatography, and electrochemistry.

This invention relates to a spectroscopic analysis known as Raman spectroscopy. Raman scattering involves the inelastic scattering of light by vibrational modes within a molecule. This can be very advantageous as no two molecules exhibit exactly the same Raman spectrum. This makes it possible to distinguish between similar components in a mixture.

This advantage in specificity associated with Raman spectroscopy is overshadowed by an inherent lack of sensitivity. Typically about one in a million photons of light incident on a sample will take the form of Raman scattering. In practical terms Raman is limited to about one part in a thousand detection levels when the analyte is in a matrix.

The Discovery of Surface Enhanced Raman Scattering

Surface enhanced Raman scattering (SERS) like many scientific discoveries, evolved out of serendipitous events. In the early 1970's electrochemists began using optical methods to study electrode surfaces. Flieschmann and Hendra decided to experiment with Raman spectroscopy as a method of analyzing electrode surfaces. Due to the low sensitivity of Raman spectroscopy they chose silver as the electrode material since it is easily roughened by oxidation-reduction cycles in the presence of chloride. The growth of silver chloride crystals and reduction back to silver leads to a roughened surface with many times the surface area of a smooth polished electrode. This will increase the Raman signal as there are more molecules in the laser beam. They chose pyridine as the probe molecule as it should adsorb through the pyridine nitrogen and it is an inherently strong Raman scatterer. Their experiment was a success. They did not know it but this was the first experiment using SERS. It was not until four years later that this experiment was correctly interpreted. In 1977 Van Duyne at Northwestern University was also trying to study electrodes with Raman spectroscopy. His approach was to use resonantly enhanced molecular probes to overcome the sensitivity problem. He had performed calculations to determine the amount of resonance enhancement needed to observe a monolayer on an electrode. This number was at least 1000 for a strong scatterer like pyridine. This made Flieschmann and Hendra's results look anomalous. To test if the enhancement was due to increased surface roughness Van Duyne's student David Jeanmaire tried a milder oxidation-reduction cycle and achieved even stronger signals. This lead to the first announcement of an anomalous phenomena at silver surfaces.

It is now known that the SERS effect arises through an electromagnetic resonance that can occur strongly in noble metal particles and to a lesser extent in some other metals. The resonance occurs because the electrons in the particle are affected by the excitation light to produce a polarization in the particle that makes it more likely to become more polarized. This phenomenon will produce very large electric fields near the particle surface and thus amplify optical events near the surface that are dependent on the electromagnetic field. Raman scattering is just one class of such events. Others might include fluorescence and absorbance. Further, each may be enhanced through a surface phenomenon as in the case of surface enhanced Raman spectroscopy.

While SERS was discovered on electrode surfaces, it is not limited to these. Today SERS is being performed on evaporated metal surfaces, etched metal foils, microlithographically produced surfaces, carefully assembled particle arrays, colloidal suspensions, and with other methods that are capable of producing small submicron sized particles. An excellent discussion regarding aspects and uses of Raman Spectroscopy in a detection context is contained in the document "Method and Apparatus for Detection of a Controlled Substance", International Application Published Under The Patent Cooperation Treaty (PCT), WO 98/59234, United States National Stage Application No. 09/446,168.

Several problems have plagued the development of SERS into a practical analytical tool. One such problem is the delicate nature of the SERS substrate. The SERS phenomenon is associated with particles or roughness features that are about $\frac{1}{10}$ the size of the wavelength of the light used for excitation. Typically this means 40 to 100 nanometers (a nanometer is one billion of a meter). Particles this size are very susceptible to chemical damage, aggregation, and photo damage.

A survey of the different SERS substrates produces one type that stands out with respect to practical analytical chemistry. These are colloidal suspensions. Two significant advantages are found with colloidal suspensions. First, a large volume of colloidal particles can be made at one time. Within this batch of colloids every sample will be identical. This overcomes the irreproducibility of non free floating particulate surfaces. The second advantage is that the colloidal particles are suspended in a solution and therefore tend to be much less susceptible to thermal damage. They also are subject to Brownian motion which tends to continually refresh the particles in the excitation beam, thus eliminating problems with photodegradation of the sample.

In addition to problems with SERS substrate stability and reproducibility an additional factor needs to be included in the analysis. The SERS substrates are typically noble metal particles. The noble metals are aptly named for their ability to resist the aggressions of other materials. In a practical sense this is good for stability of the surfaces, but is impractical in terms of attracting an analyte to the surface. In order for the SERS substrate to act as a tool for detecting an analyte, it must attract the analyte to the surface or in some way be specifically affected by the analyte to show a spectroscopic response.

Initially SERS was seen as advantageous because of its strong enhancement. This invention realizes a different aspect of SERS. The localization of the SERS enhancement near the surface very effectively separates the signal from the analyte that is in close proximity with the surface from analyte or other material in the sample matrix. The locality of the analyte can be used to a strong advantage with respect to the ease of analysis. SERS allows one to measure an analyte in the presence of species that would strongly interfere and cripple other methods of analysis that do not have a localized area of detection.

The problem of inertness with noble metal SERS active surfaces can be overcome with a coating material that attracts or is affected by the analyte. Basically, this combines the strong advantages of an enhanced sensitivity from the SERS substrate with the reactivity or affinity of a molecular specific coating.

Four classes of coatings can be described for a SERS surface. These are passive coatings that can attract the analyte into close proximity of the surface through a chemical affinity for the analyte, the presence of which is detected by its SERS spectrum. Active coatings bind the analyte reversibly and indicate the presence of the analyte through a spectroscopically observable change in their chemical structure. Reactive coatings actually react with the analyte through a covalent bond and create a new species on the surface; this new species is related to the analyte and produces an analyte distinct spectrum for identification and quantitation. The fourth class of coatings are sandwich coatings that bind the analyte and with the addition of a reporter molecule produce a quantifiable signal for the analyte. The latter often consist of immunological coatings with an inherent specificity built into the coating by an organism's immune response.

A problem that exists when these coatings are combined with a SERS active surface is that the surface becomes less stable. This is particularly true with colloidal suspensions. Colloidal suspensions are stable because the colloidal particles maintain a strong electrical charge through adsorbed ions. In most SERS active systems the colloids are stabilized by the adsorption of citrate ion. This creates a strong net negative charge on the particles and makes them repel each other in solution. Without this net charge the particles would rapidly coalesce into a SERS inactive aggregate of colloidal material.

When coatings are applied to the active colloids it is often impossible to displace the citrate or if the citrate is displaced the colloids begin to aggregate and fall out of suspension in a short time. In some instances it is necessary to add stabilizers of some type to increase the lifetime of the colloids; however, over long periods of time the effectiveness of these stabilizers may be insufficient. It would be commercially desirable to produce a colloidal SERS active system that contains a coating specific for an analyte which had long term stability. Such an invention would have tremendous advantage as a quick and easy to use method for chemical analysis.

SUMMARY OF THE INVENTION

The present invention includes a variety of aspects which may be selected in different combinations based upon the particular application or needs to be addressed. In one basic form, the invention discloses the use of Raman spectroscopy to analyze colloidal particles that have been specially prepared to have long term stability and to be sensitive to a specific analyte or group of analytes. A specific advantage of this approach is that the SERS phenomenon exhibits a signal from material localized near the particle surface. This precludes the need for removing excess analyte, impurity, or reagent that indicates the presence of an analyte from the sample mixture. This aspect combined with the aspect of a coated particle with long term stability leads to the invention of a commercially important one-step assay.

This invention includes aspects of colloidal preparations that can be stored for long periods of time and reconstituted to a SERS active suspension. A particularly important aspect of this is the amount of colloid is determined very accurately though a volumetric delivery of known concentration or delivery of a known mass of colloidal suspension. The mass delivery is enabling to an assay since a large mass of diluted colloid can be used to accurately deliver a small amount of colloid into a sample chamber.

The preparation of the colloidal assay potentially includes pretreatment of the sample chamber to prevent the colloidal particles from binding to the surface or each other. This aspect may also include the use of a sample container that naturally possesses the ability to contain the colloids without affecting their ability to be reconstituted.

The configuration of the test materials in the sample container is an important aspect of this invention. Many of the assays covered under this invention will use reagents that should be added in a sequential fashion. This could be carried out with a one-step addition of sample if the different reagents are placed in matrices that control their rate of release, though in many cases controlled release may not be necessary.

The invention also includes aspects of the colloid particle nature that allow a coating to easily displace a prior coating on the colloid formed during preparation that is present for stability.

In keeping with our goal of designing an assay system that has long term stability such that a pretreated assay could be produced for the customer for later use, the invention includes a sample container design that incorporates these features. Assays are typically performed both individually or multiply. Multiple assays have an advantage that many of the steps involved in the assay can be performed in parallel thus decreasing the time of assay. This invention describes a sample chamber that can be easily fabricated in a multi-sample format. Additionally, as our assay takes special advantage of the SERS effect to produce a one-step assay the sample containers can be sealed to prevent contamination of the sample or, more importantly, prevent potential spread of the sample which may be hazardous to the testing personnel or facility.

Naturally, further objects of the invention are disclosed throughout other areas of the specifications.

Example of a prototypical desiccated colloid assay. The assay preparation begins with the addition of metal particles to the sample container. The particles are then coated with the molecule specific coating. This is followed by drying the molecule specific coated metal particles. At this stage additional reagents my be added for the analysis. For example, a reporter may be added and a second desiccation performed. After the final desiccation the sample container may be stored for long periods of time prior to reconstitution with the sample. After reconstitution with the sample the analysis is performed by acquiring a Raman spectrum of the material in the sample container.

FIG. 2

Figure 2:
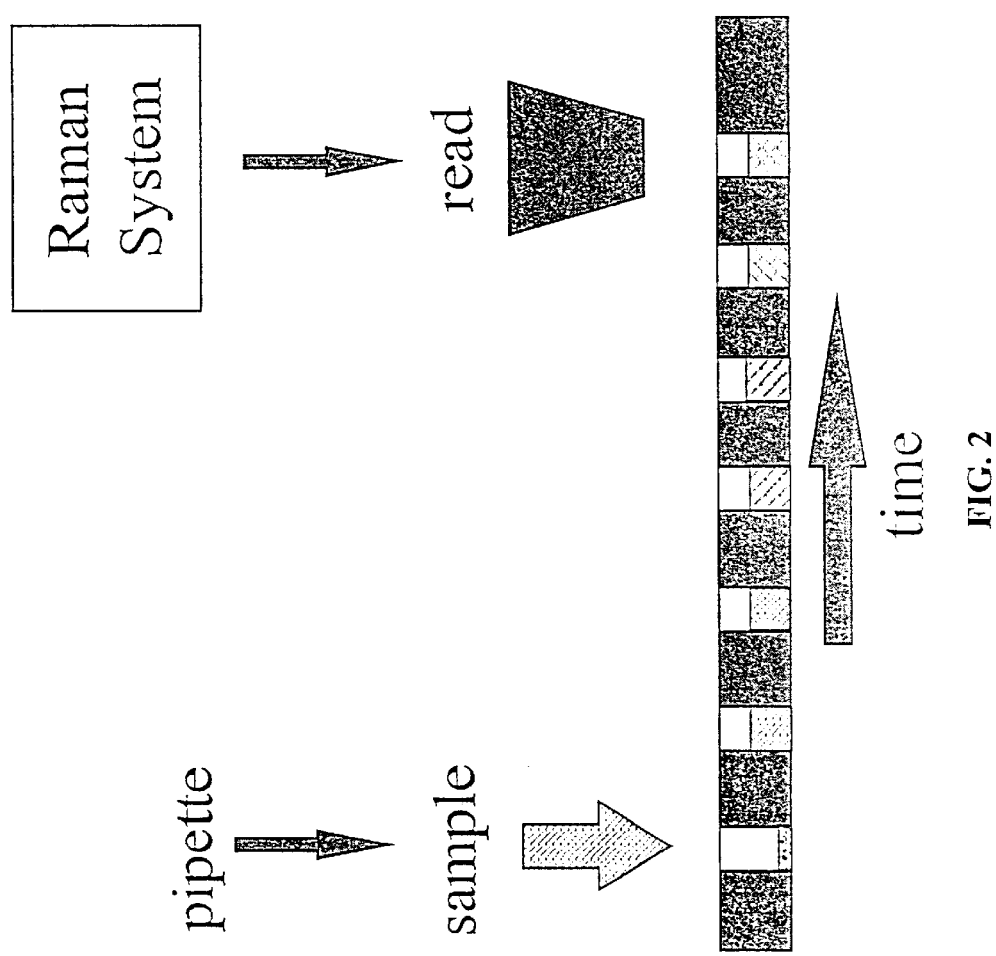

The instrument for the analysis may appear as in FIG. 2. The sample is added by a volumetric or mass addition to the sample containers to reconstitute the analysis material. Over time the analysis material is reconstituted and interacts with the analyte. After a sufficient amount of time it is read as a Raman spectrum.

FIG. 3

Figure 3:
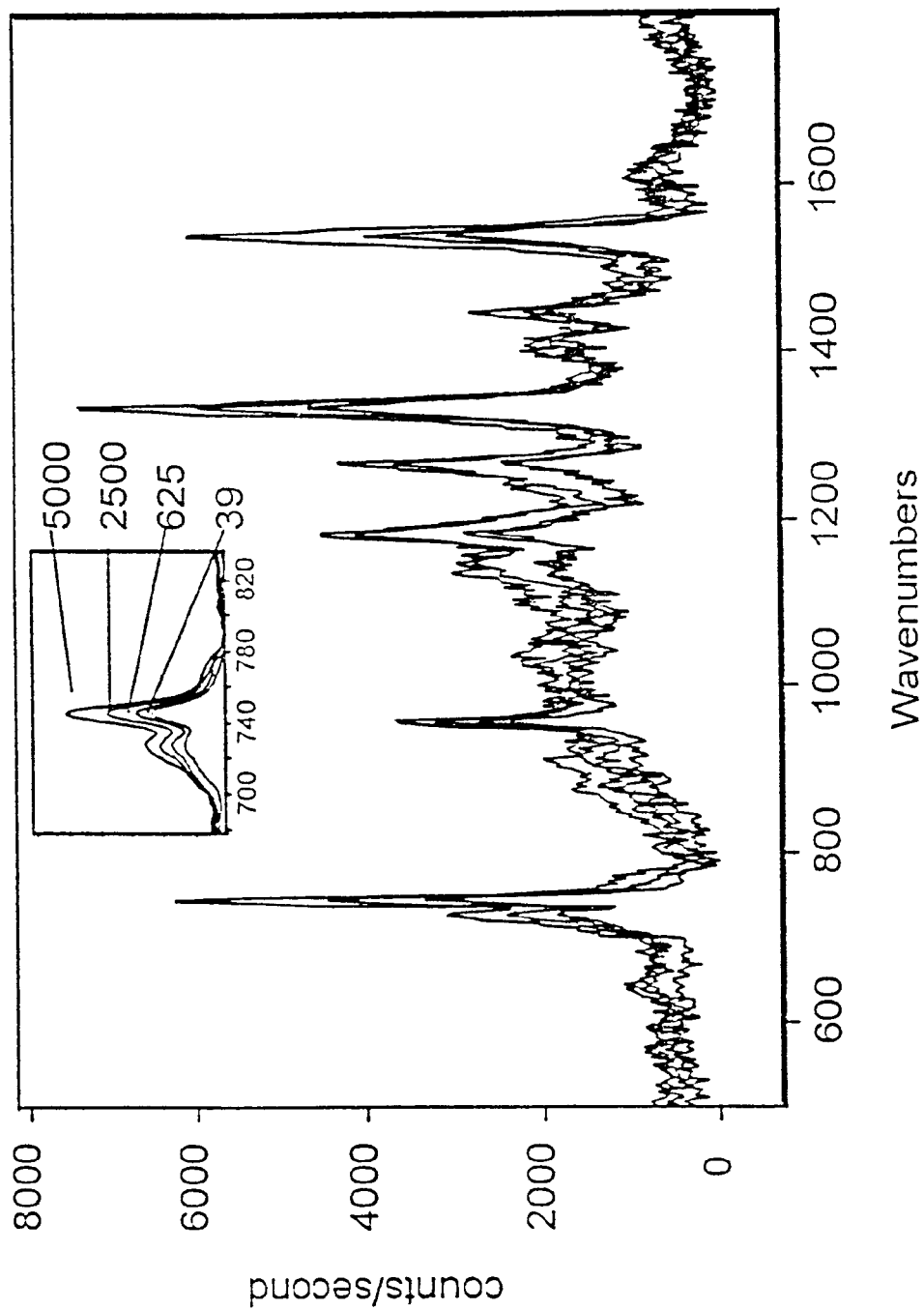

The data from an analysis may appear as in FIG. 3. This figure contains Raman spectral data for a sandwich type immunoassay of Polychlorinated Biphenyl (PCB). In this case, the bottom antibody was polyclonal specific to PCB and a nonspecific antibody (BSA) tagged with reactive blue on top. The spectra consist of many peaks that correspond to the dye material conjugated with the reporter antibody. This figure shows an insert that expands the spectral region around 700 to 800 $cm^{-1}$. The numbers to the right of the insert (39, 625, 2500, 5000) report the concentration of PCB in the sample used to reconstitute the coated metal particles. It is clear that the signal of the dye attached to the reporter antibody increases with increasing concentration of PCB.

FIG. 4

Figure 4:
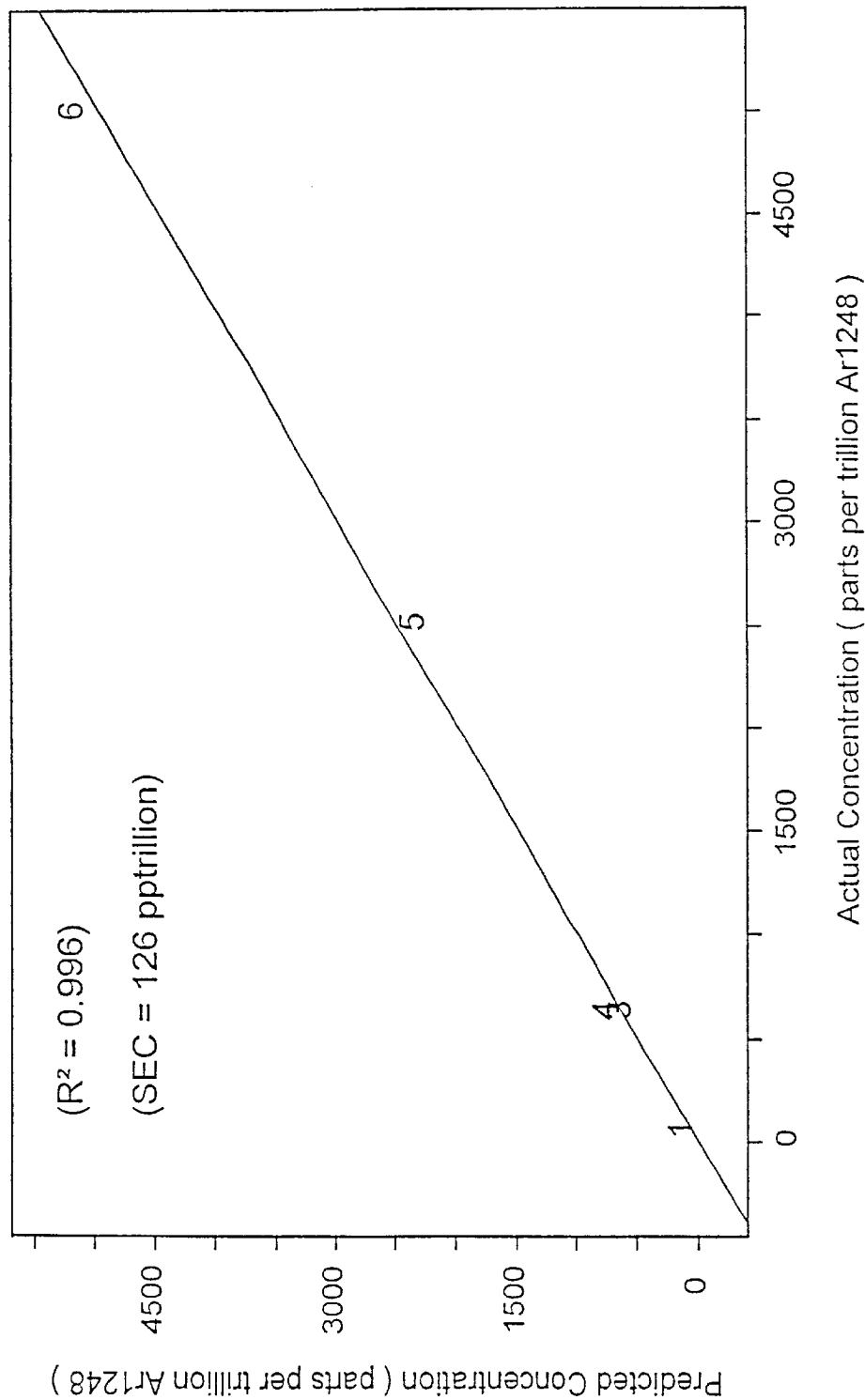
Figure 5:
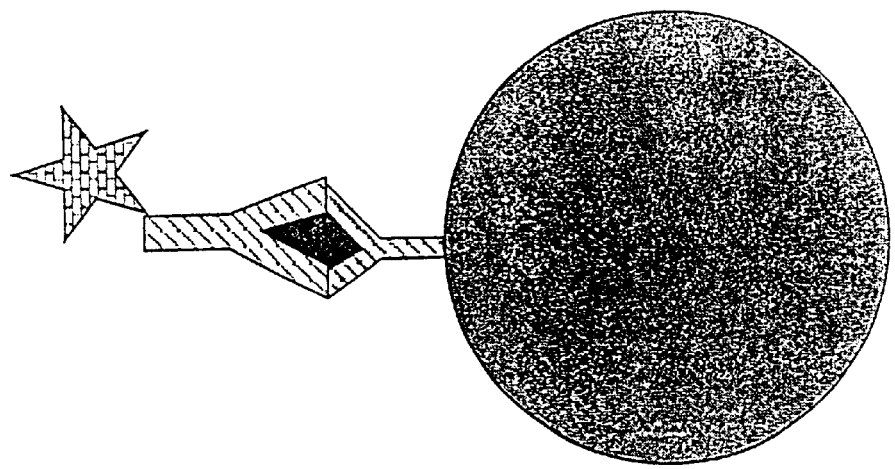
Figure 5:
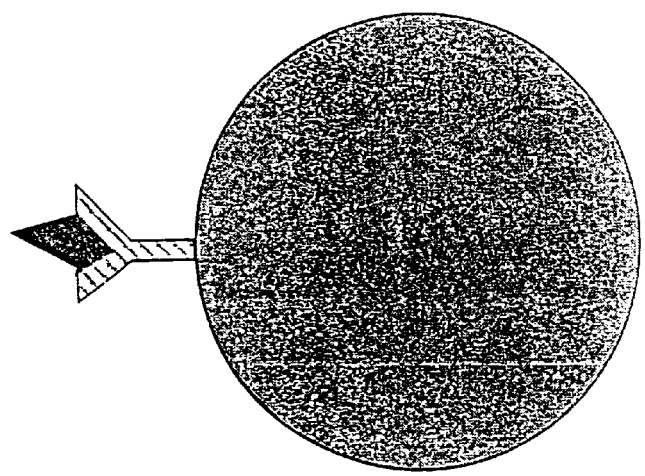
Figure 5:
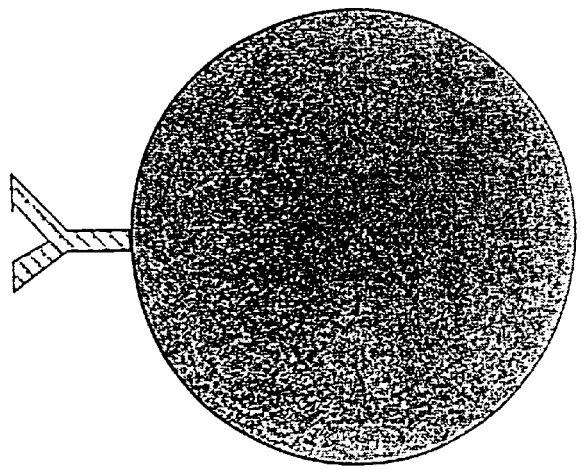
Figure 6:
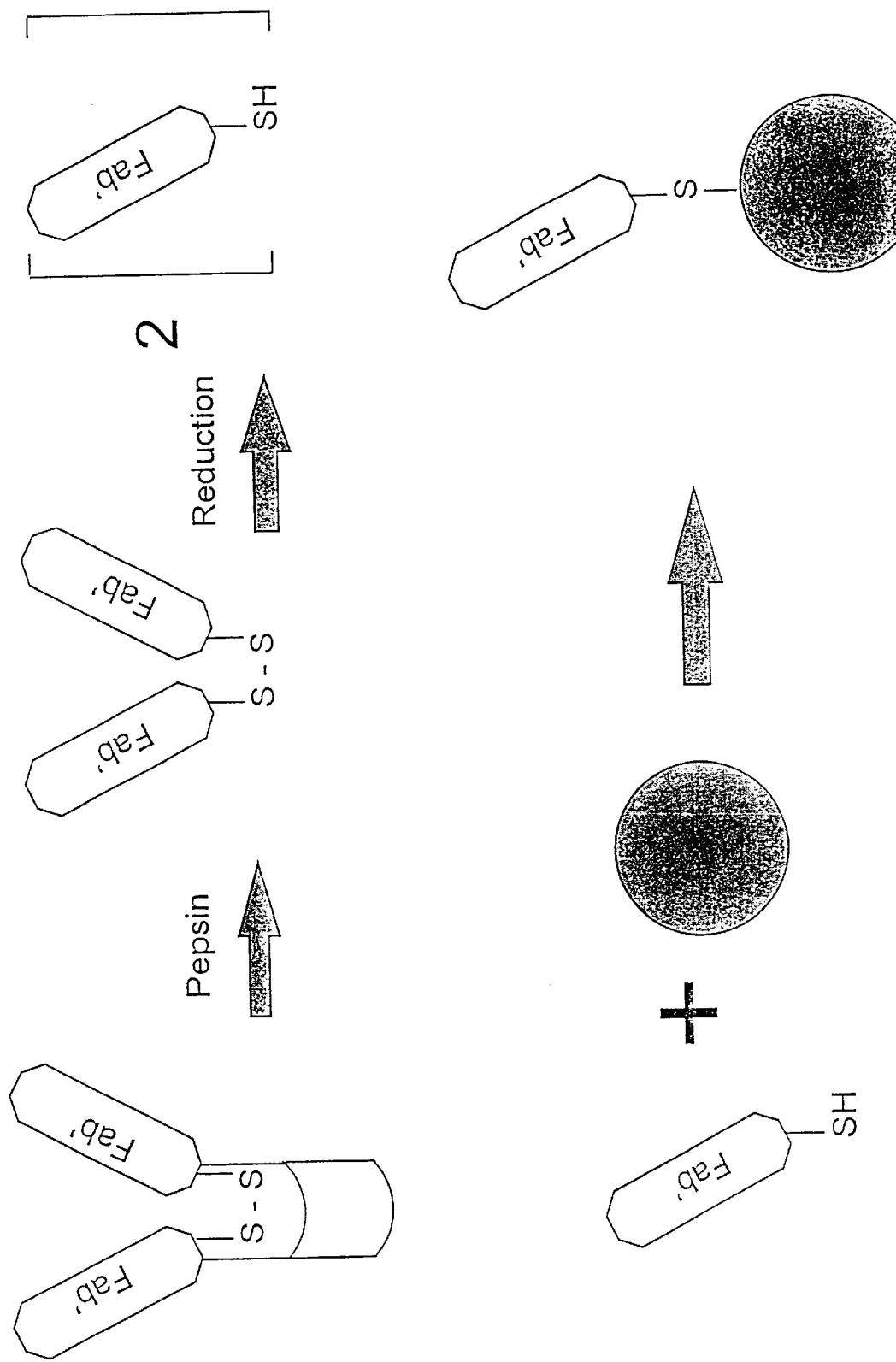
Figure 7:
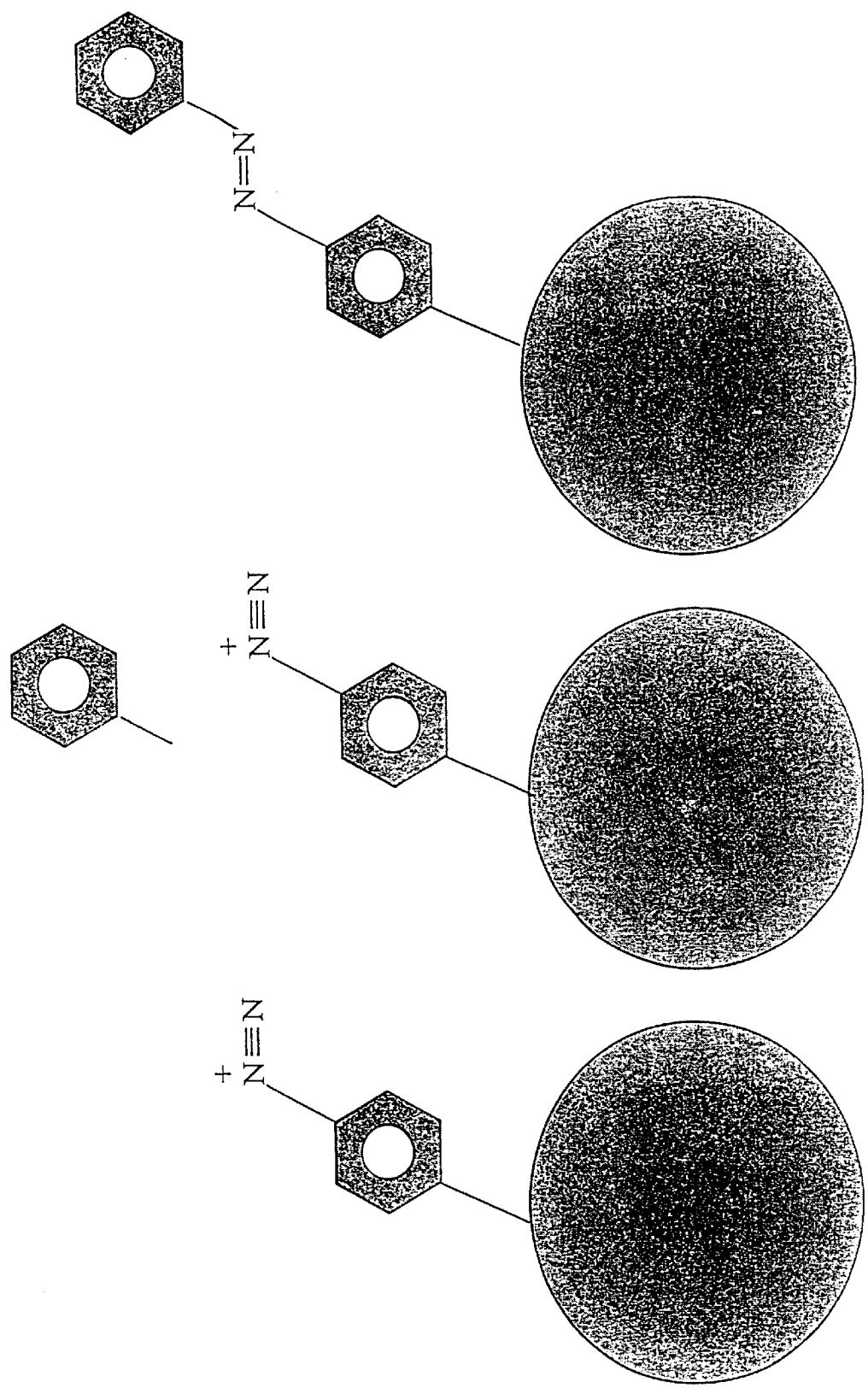
Figure 8:
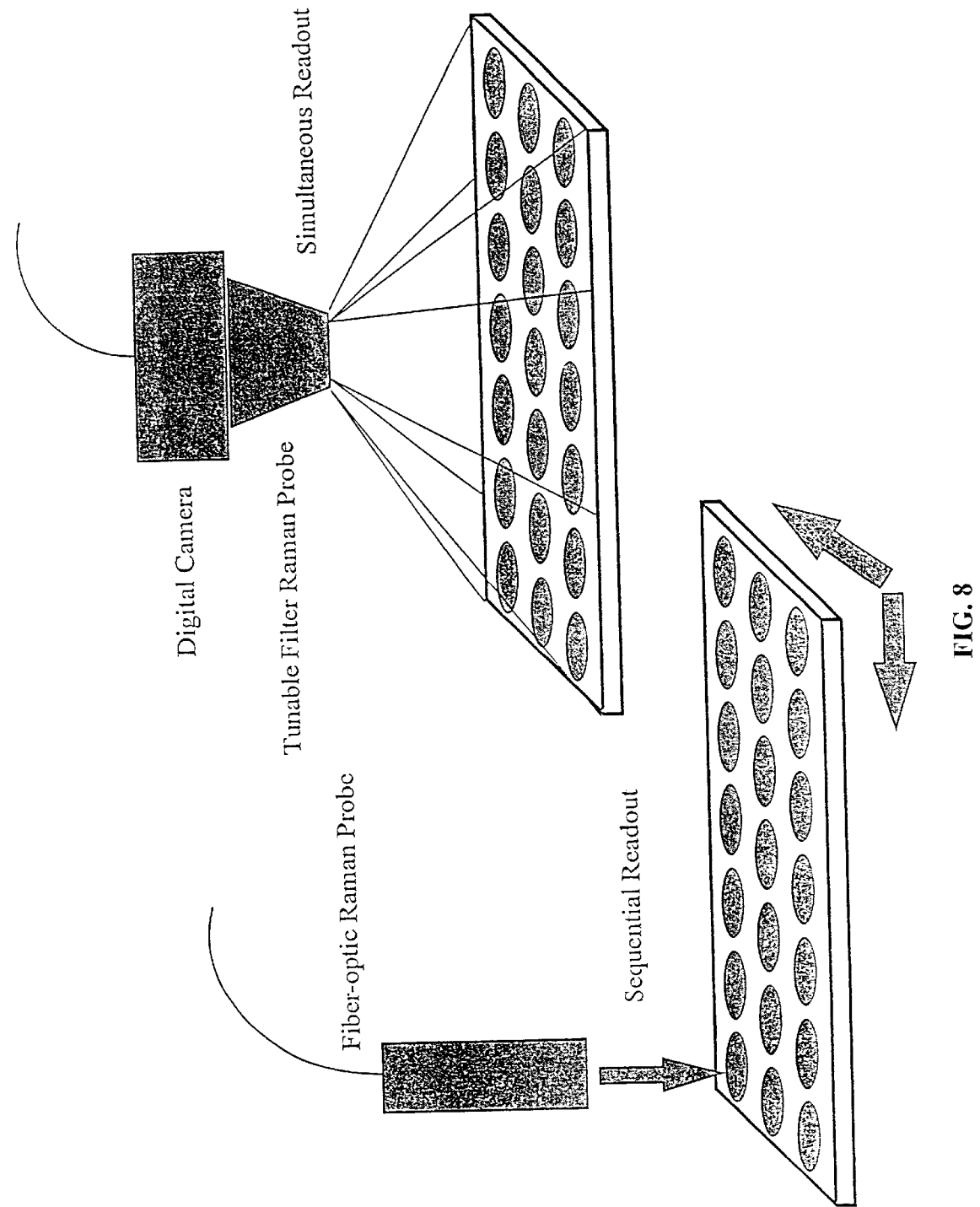
Figure 9:
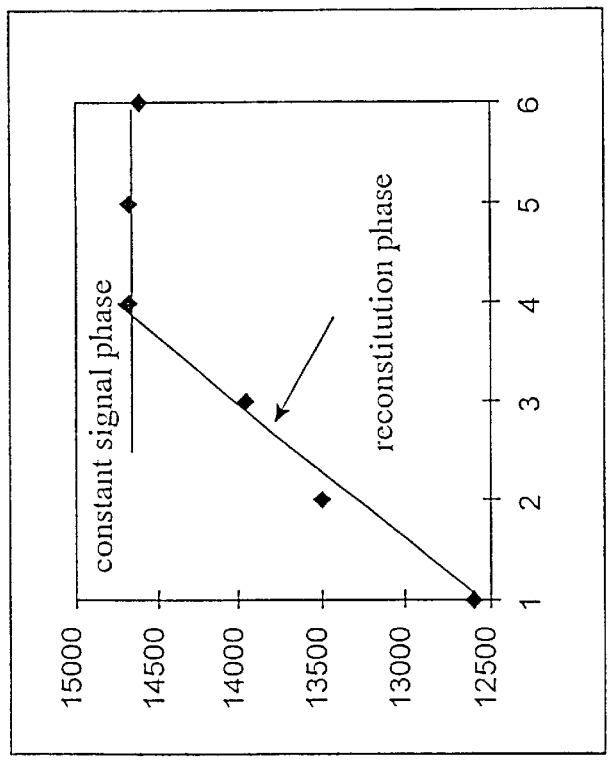
Figure 9:
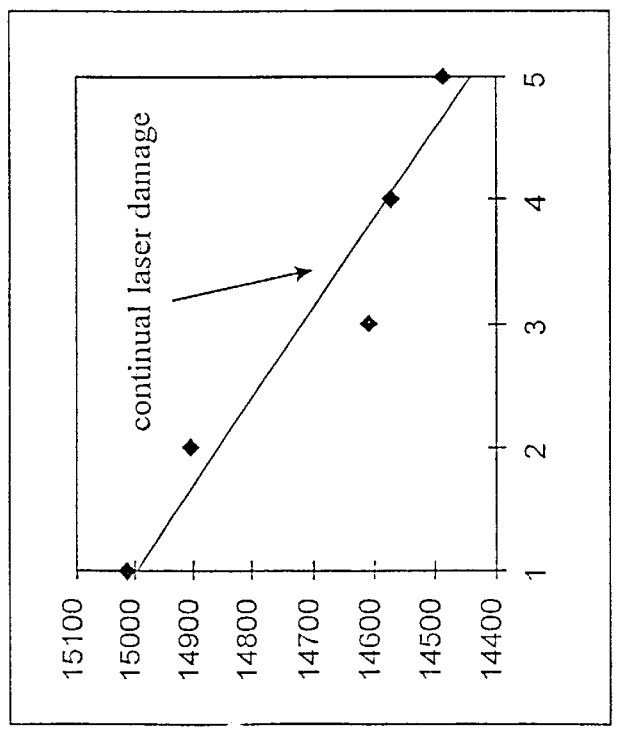

A chemometric model of the data from FIG. 3 is shown in FIG. 4. The plot in FIG. 4 was created with a chemometric algorithm described as PLS. The plot consists of predicted concentration of PCB vs actual concentration. The $R^2$ value reported at the top of the FIG. relates to how well the predicted concentration correlates with the actual. In this case, the correlation is near perfect (1.000 would be perfect). This indicates a very good model. The precision of the model is reported as the SEC (Standard Error of Calculation). The SEC in this case is excellent (126 pptrillion).

FIG. 5

Diagram of a colloidal immunoassay with an antibody attached to a colloid. This is followed by attachment of the antigen. Finally the attachment of a reporter (dye-tagged antibody) on top.

FIG. 6

A possible improvement on the common sandwich assay. In this case, the antibody is fragmented with Pepsin to produce a pair of (fab')s. These might be added to a metal particle solution to produce a fab' coated metal particle. The potential advantage may be close proximity to the metal surface, and therefore, a larger surface enhancement.

FIG. 7

Another example of a desiccated metal assay. In this case, the reactive coating is not immunological. It is a reactive chemical species that is capable of reacting with the analyte. The analyte is detected as the new chemical species on the surface. In many cases it will be desirable to design the coating such that it produces an analyte adduct that will be resonantly enhanced.

FIG. 8

Potential readout schemes for assays with desiccated colloids. Lower left represents a sequential readout scheme where each sample container is read individually. Upper right shows a scheme by which all samples of a multisample container could be read simultaneously. The second scheme could provide a significant advantage with respect to the time of assay.

FIG. 9

An example of laser damage causing an irreversible loss of signal on desiccated colloidal silver (left). This indicates that a sample consisting of a two-dimensional layer of colloids or a solid metal surface is not suitable for use as an assay. Conversely when reconstituted as a particle suspension, the signal from the colloid briefly increases and levels off to a constant value without laser damage.

DETAILED DESCRIPTION OF THE PREFERRED EMBODIMENTS

As can be easily understood, the basic concepts of the present invention may be embodied in a variety of ways. It involves both techniques as well as devices to accomplish the appropriate technique. In this application, the techniques are disclosed separately and as part of the results shown to be achieved by the various devices described and as steps which are inherent to utilization. They are simply the natural result of utilizing the devices as intended and described. In addition, while some devices are disclosed, it would be understood that these not only accomplish certain methods but also can be varied in a number of ways. Importantly, as to all of the foregoing, all of these facets should be understood to be encompassed by this disclosure.

Figure 1:
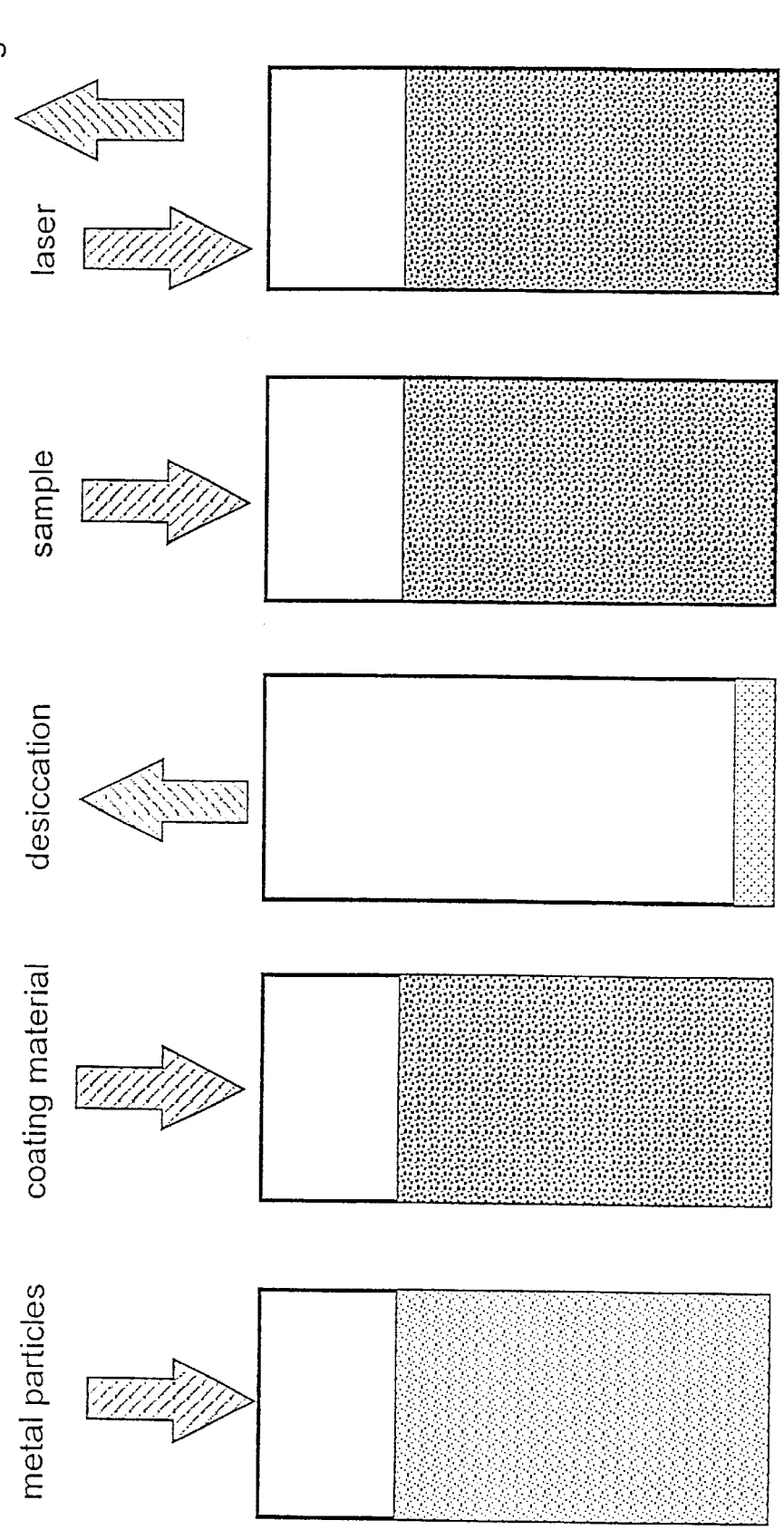
FIG. 1

Application of the detection method will involve a number of steps, each of which may have certain characteristic features, depending on the specifics of the application. The overall process is illustrated diagrammatically in FIG. 1. A source provides radiation that is altered by the sample, the radiation is transmitted to the sample by an optical path, the sample is interrogated through a probe, the probe may contain an internal reference, the modified radiation is transmitted back though an optical path, the modified radiation is analyzed through an optical analyzer, it is detected by an optical transducer, the output of the optical transducer is analyzed with a data processor and reported as information to the user. Aspects of each of these steps are detailed below.

Source

The analysis can be thought of as beginning with a source of radiation. The source must have certain characteristics. These are a narrow bandwidth and a high degree of brightness. The narrow bandwidth is needed as the measurement is made by measuring small energy changes in the source. These are manifest as bands of radiation at lower energy than the source energy and can only be observed as bands if the source itself is composed of a narrow bandwidth.

The amount of light that is modified by the sample is a small fraction of that incident on the sample. In order to detect this light with any degree of accuracy the source must be fairly bright. Currently, these characteristics of the source are almost exclusively fulfilled by the use of laser light as the source. One could, however, envision a source composed of a very bright polychromatic or monochromatic radiation output that could be filtered to produce a degree of monochromacity and focussed to produce a usable brightness.

Optical Path

The optical path describes a means to transmit the source radiation to the sample and to collect the modified radiation from the sample and transmit it to a spectral analyzer.

The light can be transmitted to the sample by two means: a beam of light, or light contained in a waveguide. The light beam is produced by an optical transducer designed to transmit light from a source, usually a laser, over a distance to the sample. In between the transmitting transducer and the sample there is usually one or several optical transducers that transform the transmitted beam into a focussed spot at the sample. In addition, there is often a filter to remove spurious features prior to sample excitation.

After excitation the source radiation is modified by a shift to longer wavelengths, a different spatial distribution, and the amount of modified radiation is very small in comparison with the original source. This light is collected by a collection optical transducer and sent to the spectral analyzer. Often, prior to sending the light to the spectral analyzer, it is filtered to remove residual source radiation. This reduces or eliminates the formation of spurious features in the path to the spectral analyzer. Prior to the spectral analyzer there is often a focussing transducer that efficiently couples the light into the spectral analyzer.

The use of waveguides usually includes the optical elements described above. The waveguides are often in the form of an optical fiber. These simplify mechanical design by containing and transmitting beams without the need for a well defined linear optical path. In many cases the waveguide acts as the entrance slit to the spectrograph and thereby defines the spectral resolution of the system.

Colloids

As described in our background section many methods exist for enhancing Raman scattering by means of the SERS effect. This application utilizes these substrates as a means of enhancing a signal from a coating material. Of the possible SERS methods colloids perhaps show the greatest potential.

Colloids are small particles that can remain suspended in solution long enough for an analysis to be made. Several aspects of colloids make them the system of choice for an analysis using coatings. First, a viable SERS analysis system must have a SERS substrate that is reproducible. The irreproducibility of the SERS system limits the precision of the measurement. Planar SERS substrates such as an electrode or foil are very difficult to impossible to make reproducibly. Colloids on the other hand are made by chemical reactions on a very large scale and it is possible to make a batch of colloids that could last a very long time and have excellent consistency from sample to sample. Furthermore, as the procedure uses large amounts of materials it is easy to reproduce the procedure to have very good batch to batch consistency.

In addition to consistent enhancement by a batch of colloids, it may in some cases be essential to have the same amount of colloid in each sample container. This may be done by weighing a dried colloid preparation or a centrifuged slurry. However, the amount of colloid required for each sample is very small and weighing would lead to inaccuracy. This invention describes an enabling method for depositing a known amount of colloid in each well. This could be done by adding a known volume of colloidal suspension and drying the suspension. The significance of this can be seen from a calculation. We use 90 mg of silver nitrate to 500 mL of water to make the colloid. A 5 $\mu$L sample container will take 900 ng of colloid. It is difficult to impossible to weigh out 900 ng, but the volumetric addition of 5 $\mu$L can be performed accurately.

As this invention describes the uses of a coated colloid for analysis, it may be necessary to fabricate colloids that can easily accept a coating. The colloids remain stable in suspension due to their coating of charged material. The ease or difficulty with which this material can be displaced varies with the type of colloid preparation. This invention describes the use of colloidal preparations that may produce particles with weakly bound charged material that can be displaced by our coating material.

Colloids also have an advantage of heat dissipation and continual replacement. SERS measurements are made difficult and are limited by the amount of radiation that can impinge on the surface before damage is done by localized heating or a photochemical process. Since colloids are suspended in a solution they can withstand quite high laser powers without heat damage. The three dimensional solution matrix very effectively removes heat.

Additionally, one of the mechanisms by which colloids stay in solution is through Brownian motion. Brownian motion describes the random motion of particles in a solution or gas by collision with solution or gas molecules. In the case of colloids, this means that they are constantly moving and will move in and out of the laser beam during the analysis. This continually refreshes the sample in the beam and in effect reduces the possibility of signal deviation due to photoeffects.

Colloids are stable for a period of time due to their electrostatic charge. This charge is of the same polarity for each colloid and keeps them from aggregating with each other. Colloid suspensions do not always exhibit long-term stability, however; aggregation or association of the colloids may occur to give particles that do not give the SERS effect, that give a greatly weakened SERS, or that may precipitate. For this reason stabilizers are sometimes added to the liquid colloid suspensions to decrease this tendency to associate, as described in Tarcha et al. U.S. Pat. No. (5,266,498).

In addition to the attractive features of colloids discussed above, colloid suspensions have unattractive features. Liquid suspensions of colloids may be impractical for many purposes of commercial importance. If a container having a colloidal suspension is tipped or turned over, some of the colloids will coat the walls or lid of the container. If a sample is then added to such a container, the amount of colloids or coated colloids that the sample encounters will be different than that in a container that has not been tipped, or has been tipped to a different degree. This variability may lead to poor estimates of the amounts of an analyte present in the sample, and poor reproducibility. Since tipping and agitation are likely to be encountered in shipping of any kind, this liquid-like behavior of the colloids is undesirable.

Those familiar with the use of surface enhanced Raman spectroscopy have attempted to avoid the problems associated with the liquid suspensions of colloids in a number of ways. These include immobilization of the colloids in a sol-gel matrix and immobilization on a number of types of surfaces, including cellulosic materials and glass. However, while these methods solve many of the problems assorted with transport and handling of colloids, they suffer from other problems: diffusion in sol-gels may be slow and/or nonuniform, while immobilization on a surface requires careful focusing to obtain spectroscopic measurements of good quality. All of these types of immobilization also suffer from the problems of localized heating due to irradiation during focusing and acquisition of the spectrum; this localized heating is avoided in suspensions of colloids in liquids.

If the liquid colloid suspension could be partially or completely desiccated to give a residue that was substantially immobile, the transport and handling problems associated with liquid suspensions can be avoided, since tipping or shaking would not likely result in dispersing the colloids on the interior of the sample container in a random fashion. Reconstitution of the colloid with a liquid would then give back a colloid suspension having all of the advantages associated with the original preparation.

Workers in the field of analytical chemistry and analytical chemistry as applied to surface enhanced spectroscopic techniques involving colloids have not taken advantage of the benefits that can be afforded by desiccated colloids. This is because it is common knowledge that desiccating a colloid irreversibly alters the desirable characteristics that make the colloids useful for surface enhanced spectroscopic analysis techniques. This irreversible alteration results from the association and aggregation of colloids that occurs when water is largely removed from the suspension. The resulting silver particles usually exhibit no, or extremely reduced surface enhancing spectroscopic characteristics. The outer, charged surfaces of colloids also promote their adhesion to the surfaces of containers commonly used for the SERS measurements. This problem can be even more severe for colloids coated with analyte binding agents (for example, antibodies); thus, while some colloids are prepared by a process which involves filtering the colloids to, or near dryness, and then reconstituting with a liquid, colloids which are coated with many substances cannot be successfully reconstituted. The fact that desiccation of colloids, and especially colloids coated with binding agents, destroys their desirable characteristics is so well known that even workers accustomed to stabilizing liquid colloid suspensions, and who are aware of the immobilization of colloids in sol-gels and on surfaces have not apparently attempted to produce desiccated colloids One key to this invention is the use of a sample container coating that prevents tight adherence of colloids and colloids coated with binding agents to the surface of the container. Such coatings may be hydrocarbons that do not adhere strongly to colloids. For example, a paraffin material has been used as a coating for a sample well for drying colloids. Other examples include oxygenated analogs of hydrocarbons (such as polyethers and polyalcohols), organosilicon species and their oxygenated derivatives, as well as halocarbons, including perfluorocarbons such as Teflon. In some cases it may be possible to avoid the necessity of prior coating of the container by including the reconstitution agent with the suspension of colloid and desiccating the mixture. It may be possible to use coatings on the surface of the container which possess the same type of charge (usually negative) as that on the colloids so as to repel the colloids from the surface.

It may also be desirable to place the colloidal particles in a matrix that prevents aggregation. Such a matrix might be a gelatin like material that does not allow rapid motion of the colloids, but which can be easily dissolved by the reconstituting liquid. Another example might be an enzyme digestible matrix to contain or support the colloids. In this case, the enzyme could be added with the sample or dried into the sample container in such a way that it is activated by the sample. The key difference between these matrix stabilized colloids and other methods of stabilizing colloids (in sol-gels or on surfaces) is that the matrix is dissolved upon reconstitution with a liquid, so as to return the colloid to it's solution-like behavior.

It may also occur that the process of coating the colloids with the analyte specific coating will naturally produce colloids that can be dried and reconstituted without the addition of a matrix or the use of special sample containers. Colloids may be coated with an inert coating to prevent aggregation without a special matrix or sample container. Such coatings whether analyte specific or not would be included as enabling technology in this patent.

The ability to dry and then reconstitute colloids having a wide variety of surfaces enables a sample container or plate (collection of sample containers) to be prefabricated with colloids or modified colloids. For example the current 96 well or higher microwell plates could be modified for use with the assays described in this invention. Such a prefabricated sample or plate could be stored for extended periods of time and then be reconstituted by addition of some liquid which contained an analyte of interest, or through sequential addition of some liquid followed by the analyte itself, or the analyte dissolved in some liquid.

Sample Container

The sample container in this case constitutes a container that contains a SERS surface and into which the sample is placed. Most likely the sample container will contain a coating of dried colloidal particles and may contain a film of dried modified colloidal particles or powdered modified or unmodified colloidal particles.

Several unique aspects of the sample container are contained in this invention. Many of the applications that this invention will address are testing of biohazardous materials or toxic chemicals. Most current methods of analytical chemistry for these samples require steps to wash away excess reagents. This washing step amplifies the amount of hazardous waste and exposes workers to hazardous materials. The invention described herein utilizes the SERS effect to make the assay specific to material present at the SERS surface and, therefore, does not require material from solution to be washed away. This is a very significant advantage and can be further enhanced by the design of a sample container that takes advantage of the no wash benefit.

The sample container in this invention will contain the possibility of a cover to prevent transference of material to the invention operator or the environment around the device. The cover may be composed of a material that can be penetrated by a device to place the sample into the sample container, but which does not allow material to leave the sample container. For example, a simple septum type cover would serve this purpose. Other possibilities might be a gel material that is easily penetrated by the sample injection device.

The sample container may consist of a material that allows the dried colloidal particles to be reconstituted. Materials such as teflon or what is generally classified as low energy surfaces have been shown to possess this characteristic.

Similarly, the sample container may be coated with a material that allows the colloidal particles to be reconstituted. Typically, sample containers are plastics such as polystyrene. We have found that such containers tend to not release a dried colloidal suspension when a reconstitution is attempted. However, coatings such as teflon or hydrocarbon coating do allow the colloidal particles to become free from the surface.

SERS Coatings

The SERS coatings in this assay describe material that are coated onto the SERS substrate to bring the material that is to be detected into close proximity with the SERS surface. These coatings include passive coatings that simply attract the analyte to the surface, active coatings that change their Raman spectrum in the presence of the analyte, reactive coatings that bind the analyte to form a new surface coating that may be characteristic of the analyte, and sandwich coatings that bind an analyte to form an adduct. The adduct is then detected by the addition of a reagent that caps the adduct and which contains a Raman active group for identification and quantitation, or addition of a reagent or substance which changes or enhances some spectroscopic feature present in the analyte or in the surface coating (e.g., fluorescence quenching or enhancement).

These coatings can be applied to the surface by any means that cause reasonable adhesion. A preferred method would be to use a chemical group that strongly binds with the colloidal material. For example, a sulfur group (thiol or disulfide) is known to bind strongly and has been used to produce coatings on SERS substrates.

Assay Methods

Assays can be performed with this invention by the addition of the sample to a sample container that contains a film of dried colloid or dried modified colloid. This enables the manufacturer of the sample containers to make a one-step assay kit requiring only the addition of the sample and reading by the optical analyzer, or the sequential addition of a liquid which may or may not include buffers or compounds which may enhance binding of the analyte, followed by the addition of analyte.

A potential advantage of this invention is a scheme for timed release of reagents. This allows reactions and assays to be performed with a one-step addition of sample, yet maintain a sequential addition of reagents. For example, one could have a slow release reporter in a sample container of antibody on colloid. The sample addition leads to binding of antigen with the immobilized antibody on colloid, and this is followed in time by the release of reporter and binding of reporter on top of the antigen/antibody complex. In other embodiments of this invention, controlled release may not be necessary.

This is contrasted by the current methods which require multiple steps to remove sample impurities and excess reagents for an assay. This advantage comes from the unique surface localized signals from the SERS effect and the use of dried colloids described in this application.

If the colloids are not dried for long term storage, their stability is not such that a one-step device would be possible. Since this invention is capable of using the sample to reconstitute the colloids, there is no dilution of the colloids by the sample, although this one step procedure may not in all instances be preferred.

Several assay methods are discussed in the examples section of this application. Assays typically involve colloids pretreated with a molecule specific coating. In the case of a passive coating this may be a coating such as propanethiol. The propanethiol covers the surface and creates a hydrophobic coating on the colloid. This follows the chemical principle of like attracts like and, therefore, the coating attracts hydrophobic molecules such as aromatic hydrocarbons. Similarly, an antibody coating could be used to bind an analyte and the presence of the analyte could be detected by analyte related changes in the spectrum.

Active coatings can be used as an assay for materials such as illicit drugs. In this case, a coating might have a similar chemical structure as the analyte with an opposite charge to promote ion-pairing. Detection of the analyte is made through changes in the Raman spectrum of the coating. Another possibility might be a coating that can coordinate with metal ions to form a new coating material. Again, the metal ion can be detected by changes in the Raman spectrum of the coating. Similarly, an antibody coating could be used to bind an analyte and changes in the spectrum of the antibody used to detect the presence of the analyte.

Reactive coatings can be used as an assay for reactive materials such as bilirubin. Reactive coatings contain a group that is reactive toward a specific molecule or class of molecules. One such coating is a molecule containing a reactive diazonium. This coating can form a covalent adduct with a specific class of analytes that have electron rich sites. The product is an adduct that contains structural features of the original analyte that can be used for identification and quantification.

Sandwich coatings can be used with this assay to detect a plethora of toxic materials or biologically significant materials. A typical sandwich assay involves binding the analyte with a molecule specific coating on the colloid to form an adduct on the colloid. One could detect the analyte at this point through its spectrum or its affect on the coating as described above under "active coatings". Greatly improved sensitivity can be achieved by attaching a second coating that is bound to the antibody/antigen complex and is detected with particular ease by the optical source. The second coating may be described as a reporter as its function is to announce the presence of the analyte bound to the colloid. This assay makes it possible to detect a weak Raman scattering analyte through a strongly scattering reporter. This effect would be especially strong when using a reporter which is in resonance with the optical source (see below, in "Resonance Raman"). This type of assay greatly benefits from this invention as excess reporter that in other assays needs to be washed from the sample does not need to be removed in this case since this invention uses SERS which only observes reporter in close proximity with the surface. Analytes may also be detected by measuring their effects on the binding of an analyte analog which is configured so as to be detected with particular ease.

In this context, an analyte analog should be understood as including a variety of molecules and molecule types. It may incorporate structural features that allow it to be bound by an analyte responsive surface in the same, or nearly the same fashion as the analyte itself. In addition, the analyte may most commonly incorporate some spacer group or series of atoms that connect it to another subunit that has distinctive spectroscopic features. This latter subunit may be referred to as a spectroscopic marker, and the analyte can be said to be "tagged" by the spectroscopic marker. In many instances this spectroscopic marker may be a dye molecule, though this does not need to be the case. When the spectroscopic marker is a dye molecule, the analyte analog may even be referred to as a dye-tagged analyte. Further, in any embodiment, it should be understood that the marker can be included at any appropriate point in the system. Thus, by use of the term "associated", it should be understood to encompass any appropriate type of inclusion whether on the analyte, analyte analog, antibody, or other type of element. Even though the marker may be literally attached to some other element, it should still be understood as being "associated" with some other element.

In the case of an immunological assay several configurations are possible. These are explicitly described by some of our examples. For example, immunological assays are often amenable to a sandwich configuration. The first coating may be specific. A specific coating will bind a specific analyte or class of analytes. The top coating could then be a specific or nonspecific coating tagged with a resonantly enhanced dye. In the case of a nonspecific top coating this would represent a significant cost savings as nonspecific antibodies are less expensive than specific antibodies. Alternatively, the first coating could be nonspecific. This would allow it to bind a range of analytes. The second coating could then be a specific antibody tagged with a reporter. The advantage would be a product that could be used for a variety of tests, or, by having different reporter tags for a battery of specific antibodies, one could make a multiple assay in one sample container. Another possibility is a mixture of colloids treated with a variety of specific antibodies for various tests and a nonspecific reporter to announce the presence of analytes at the bound specific antibodies. Although the description above has focussed on immunological assays, it should be understood that the same principles apply to other types of coatings which involve specific interactions between either a top or a bottom coating of an analyte, regardless of whether the interaction with the complimentary bottom or top coating is specific or nonspecific.

Competitive assays are included in this invention. A competitive assay may be of the form of a coating with an affinity for a specific analyte or class of analytes. Prior to analysis, or as preparation of a pretreated plate, the coated colloids may be treated with an analyte that has been tagged with a reporter. This will, in the absence of analyte, produce a strong signal from the reporter. When an analyte is present, it will displace the bound reporter through an equilibrium mechanism and the signal will decrease in proportion to the amount of analyte present in the sample. This technique is known in immunoassay. However, it has a special significance in SERS analysis as the signal in SERS is strongly dependent on the distance from the surface (colloidal particle) and the reporter. Therefore, a competitive assay which uses the SERS methods described in this invention will benefit strongly from this spectroscopic method. Additionally, former methods of competitive assay could not distinguish between the captured reporter and that displaced by the analyte. The SERS method is sensitive to only the captured reporter and will not require washing. As described earlier, this is an enabling advantage with respect to automation and the prevention of waste enhancement through washing.

As a person of ordinary skill in the art would readily understand, it should be clear that to accomplish this method a variety of steps are possible. Orders and types of steps are intended to be encompassed by this disclosure. For example, the steps of desiccation, reconstitution, addition/interaction with an analyte analog, and addition/interaction with analyte all may be varied in numerous ways. Several of the potential possibilities include:

a) adding analyte analog, then desiccating, then reconstituting with a liquid, then illuminating, then adding analyte, then illuminating;

b) adding analyte analog, then desiccating, then reconstituting with a liquid, then adding analyte, and then illuminating;

c) adding analyte analog, then desiccating, then reconstituting with analyte in liquid, then illuminating;

d) desiccating, then reconstituting with liquid, then adding analyte analog, then adding analyte, then illuminating e) desiccating, then reconstituting with liquid, then adding analyte analog, then illuminating, then adding analyte, then illuminating;

f) desiccating, then reconstituting with analyte-analog containing liquid, then illuminating, then adding analyte, then illuminating;

g) desiccating, then reconstituting with analyte-analog containing liquid, then adding analyte, then illuminating;

h) desiccating, then reconstituting with analyte containing liquid, then illuminating, then adding analyte-analog, then illuminating;

i) desiccating, then reconstituting with analyte containing liquid, then adding analyte-analog, then illuminating;

j) desiccating, then reconstituting with liquid, then adding analyte and analyte-analog, then illuminating;

k) desiccating, then reconstituting with liquid, then adding analyte, then adding analyte analog, then illuminating;

m) desiccating, then reconstituting with analyte and analyte analog in liquid, then illuminating; and n) desiccating, then reconstituting with liquid, then adding analyte, then illuminating, then adding analyte analog, then illuminating;

Resonance Raman

An important opportunity for unprecedented sensitivity is created by this invention. If the active, reactive, or sandwich assay converts a weakly scattering analyte into a resonantly enhanced adduct or complex, the sensitivity will be greatly enhanced. Resonance enhancement occurs when the molecule being excited by the source has an electronic absorption at the wavelength of the source.

For example, a reactive coating with a diazonium group may not possess an absorption that produces a resonance enhancement at the source wavelength. The analyte may also not have an absorption at the source wavelength. However, the product of the reactive coating with the analyte could have a strong absorption at the source wavelength.

Another possible sandwich assay would be to bind an antigen to a colloid. An antibody could then bind to the antigen and the reporter could be a dye tagged antigen. Applications of this assay would be to test for the presence of antibodies to an antigen. The presence of antibodies would be seen as indicative of past exposure to the antigen.

Multiple Assays

The invention creates the possibility for multiple assays. This is possible if a range of analytes produce a unique Raman spectrum for each analyte for a given modified colloid, or if a range of modified colloids are employed.

In the case of a sandwich assay, a molecule-specific reporter can be tagged with a Raman active molecule that has a unique spectrum. A set of specific reporters, each with a unique tag, could produce a multiple assay for a given sample.

Blanks

One undesirable aspect of sandwich assays is that often the blank (a sample which is known to not contain analyte) does not fit on a line describing response and concentration. The origin of the blank discrepancy is not proven, but most likely results from a rearrangement or conformation change of the initial coating that binds the analyte. The result is that blanks give a greater response than a sample that contains a small amount of analyte.

This invention describes a method by which the problem with blanks can be corrected. The one-step aspect of the assay allows one to add a small amount of analyte to each sample container. This will place a blank on a straight line and prevent the possibility of a negative assay appearing as a false-positive.

Optical Analyzer

The energy of the Raman scattered light is determined by an optical analyzer. Two forms of analyzers are possible. One is based on interference of the scattered light with itself. This type of analysis is commonly known as interferometric analysis. This can be produced by a moving mirror or by spatially interfering the light beam. The second method of analyzing the Raman scattered light is through dispersion of the light by prisms or gratings.

There are fundamental differences between these two methods. However, both could be used for the assays described in this invention. The interferometric methods tend to use long wavelength laser sources due to the noise requirements of the detector. This significantly reduces the amount of Raman scattering. However, it may be a means to reduce inherent fluorescence in a sample.

The dispersive method does not have the constraint of long wavelengths. This tends to lead to a much better precision, accuracy, and duty cycle of the measurement. Near infrared diode lasers function very well with dispersive systems, provide rejection of fluorescence, and are compatible with optical paths composed of fiber optics.

Detector

The optical transducer is any device which converts light into an electrical signal. Common transducers are photomultiplier tubes, diode arrays, charge coupled devices (CCD) and charge injection devices (CID). Currently, the most common detector for Raman spectroscopy is the CCD device. This is popular since it has high efficiency, low noise, and allows one to acquire a complete spectrum at once.

The ability to collect a complete spectrum at once plays a crucial role in this invention. Since the invention includes monitoring several Raman features (at least one for the sample, perhaps more for multiple assays, and perhaps one for an internal standard), it is important to be able to measure these bands simultaneously. This can be achieved by moving the wavelength selective element in the optical analyzer or by using an optical transducer that analyzes several wavelengths simultaneously. The motion of the selective element requires moving parts in the system. This can be detrimental to the ruggedness of the assay device. The alternative to immobile parts is afforded by the multichannel detector is, therefore, the preferred configuration.

Analysis

The signal from an assay takes the form of a Raman peak or series of Raman peaks. The intensity of these peaks or the area is proportional to the concentration of analyte on the surface. In turn, the concentration of analyte on the surface is proportional to the amount of material in the sample.

The amount of material in the analyte can be quantitated with a calibration formed by measuring the intensity or area of the peak or peaks of interest from standard solutions and, thereby, forming a calibration curve. A particularly useful alternative to this approach is the use of Partial Least Squares (PLS). PLS recreates the sample (unknown) spectrum as a multiple of a model spectrum created by the spectra of a series of standards. The multiplication factor is proportional to the concentration.

An internal standard may be used in the analysis to normalize the data. For example, the internal standard could be a part of the coating on the colloid or a species in solution. The sample and standard spectra could be divided by the internal standard to produce a spectrum that is invariant to source power, collection efficiency, or other factors that may cause a systematic variation in the signal.

EXAMPLES

Example 1a

Preparation of Silver Colloids: Silver colloids were prepared by a modified procedure of Lee and Meisel (Lee, P. C.; Meisel, D., J. Phys. Chem., 1982, 86, 3391). Silver nitrate (90 mg) was dissolved in 500 mL double distilled water, heated to boiling while stirring. A 10 mL aliquot of an aqueous 1% sodium citrate solution was added. Boiling and stirring were continued for 1 hr during which the color of the solution changed from clear pale yellow to cloudy yellow-green. The colloid suspension was cooled and store in a Nalgene container at room temperature.

Example 1b

Preparation of Silver Colloids: Silver colloids were also prepared by a modified procedure of Carey-Lea (Carey-Lea, M., Am. J. Sci., 1889, 37, 476). An aqueous 40% sodium citrate solution (130 mL) was combined with 50 mL of an aqueous 30% iron sulfate solution. The citrate-sulfate solution was neutralized using a 10% aqueous sodium hydroxide solution. A 15% aqueous silver nitrate solution (50 mL) was placed in a 500 mL flask. With rapid stirring the neutralized citrate-sulfate solution was added to the silver nitrate. Stirring was continued for 5 min. The resulting solution was filtered to collect a purple-blue precipitate which is re-dispersed in millipore water.

Example 1c

Preparation of Gold Colloids: Gold colloids were prepared by a modified procedure of Frens (Frens, G., Natural Physical Science, 1973, 241, 20). An aqueous 0.01% $HAuCl_4 3H_2O$ solution (50 mL) was heated to boiling. To the gold chloride solution was added 0.20 mL of an aqueous 1% sodium citrate solution. The flask was covered with a watch glass and heating was continued for 40 min during which the solution turns purple in color.

Example 1d

Preparation of Silver Foil Surfaces: Silver foil SERS surfaces were prepared by first roughening 0.1 mm silver foil (99.9%) with 12 $\mu$m optical polishing paper. The roughened silver foil was then etched in a rapidly stirred 40% nitric acid solution for 10 to 20 sec. The etched foil was rinsed first in millipore water followed by an ethanol rinse.

Example 1e

Preparation of Gold Foil Surfaces: Gold foil SERS surfaces were prepared by first roughening 0.1 mm gold foil (99.9%) with 12 $\mu$m optical polishing paper. The roughened gold foil was then etched in a rapidly stirred aqua regia solution for 10 to 20 sec. The etched foil was rinsed first in millipore water followed by an ethanol rinse.

Example 2

Preparation of Human Growth Hormone (HGH) Antibody-Dye Conjugates: A 3 mM solution of erythrosin B isothiocyanate was prepared by dissolving 2.68 mg of the dye in 1 mL dimethylformamide (DMF). In a 5 mL reaction vessel 5 $\mu$L dye solution was combined with 500 $\mu$L of an aqueous solution of HGH antibody prepared by dissolving 800 $\mu$g of the antibody in 1 mL of a 1% $NaHCO_3$ solution. The antibody-dye solution was stirred at room temperature overnight. The unbound dye was separated from the antibody-dye conjugate solution using gel filtration on a Sephadex-25 column. A final solution of the antibody-dye conjugate was prepared using an aqueous 1% $NaHCO_3$ solution for a concentration of 40 $\mu$g/mL.

Example 3

Preparation of PCB Antibody-Dye Conjugates: In a 5 mL reaction vessel 5 $\mu$L erythrosin dye/DMF (3 mM) solution was combined with 20 $\mu$L of an aqueous 1% $NaHCO_3$ solution of PCB antibody (17 mg/mL) and 0.5 mL aqueous 1% $NaHCO_3$. The antibody-dye solution was stirred at room temperature overnight. The unbound dye was separated from the antibody-dye conjugate solution using gel filtration on a Sephadex-25 column. A final solution of the antibody-dye conjugate was prepared using an aqueous 1% $NaHCO_3$ solution for a concentration of 50 $\mu$g/mL.

Example 4a

Preparation of Bovine Serum Albumin (BSA) Erythrosin Dye Conjugates: A conjugate of BSA-erythrosin dye was prepared by combining 10 mg BSA and 80 µL of erythrosin dye/DMF dye solution (3 mM) in 5 mL of an aqueous 1% NaHCO$_3$ solution. The BSA-erythrosin dye solution was stirred at room temperature overnight. The unbound dye was separated from the BSA-erythrosin dye conjugate solution using gel filtration on a Sephadex-25 column. A final solution was prepared using an aqueous 1% NaHCO$_3$ solution for a concentration of 33 µg/mL.

Example 4b

Preparation of Bovine Serum Albumin (BSA) Reactive Blue Dye Conjugates: A 3 mM aqueous solution of reactive blue dye was prepared by dissolving 400 mg of dye in 100 mL millipore water. A conjugate of BSA-reactive blue dye was prepared by combining 21 mg BSA and 200 µL of reactive blue dye solution (3 mM) in 5 mL of an aqueous 1% NaHCO$_3$ solution. The unbound dye was separated from the BSA-reactive blue dye conjugate solution using gel filtration on a Sephadex-25 column. A final solution was prepared using an aqueous 1% NaHCO$_3$ for a concentration of 80 µg/mL.

Example 5

Dilution of Anti-Mouse IgG Fluorescein (FITC) Conjugates: Commercially available anti-mouse IgG-FITC conjugate is available from Sigma supplied at a protein content of 5–50 mg/mL. A working dilution was prepared using 20 µL anti-mouse IgG-FITC in 7 mL aqueous 1% NaHCO$_3$ for an approximate concentration of 14-140 µg/mL.

Example 6a

Human Growth Hormone (HGH) Immunoassay in Glass Vials: In separate 2 mL glass vials placed 100 µL HGH antibody/1% NaHCO$_3$ (20 µg/mL). To each vial containing antibody was added 100 µL HGH antigen/1% NaHCO$_3$. The concentration range of HGH antigen was 0.5 ng/mL to 1000 ng/mL. The vials containing antibody-antigen were incubated at 37° C. for 1 hr, followed by addition of 100 µL HGH antibody-dye conjugate solution (Example 2) to each vial. Incubation was continued for an addition hour at 37° C. after which 0.3 mL silver colloid (Example 1a) was added to each vial. SERS spectra were collected for each vial.

Example 6b

Human Growth Hormone (HGH) Immunoassay in Polystyrene Microwell Plate: In separate 300 µL microwells placed 50 µL HGH antibody/1% NaHCO$_3$ (20 µg/mL). To each well containing antibody was added 50 µL HGH antigen/1% NaHCO$_3$. The concentration range of HGH antigen was 0.5 ng/mL to 1000 ng/mL. The microwell plate containing antibody-antigen was incubated at 37° C. for 1 hr, followed by addition of 50 µL HGH antibody-dye conjugate solution (Example 2) to each well. Incubation was continued for an addition hour at 37° C. after which 100 µL silver colloid (Example 1a) was added to each well. SERS spectra were collected for each well.

Example 6c

Human Growth Hormone (HGH) Immunoassay in Glass Vials: In separate 2 mL glass vials placed 0.3 mL silver colloid (Example 1a) and 100 µL HGH antibody/1% NaHCO$_3$ (20 µg/mL). The vials were then incubated at 37° C. for 1 hr. To each vial containing silver colloid/antibody was added 100 µL HGH antigen/1% NaHCO$_3$. The concentration range of HGH antigen was 1 ng/mL to 200 ng/mL. The vials containing silver colloid/antibody-antigen were incubated at 37° C. for 1 hr, followed by addition of 100 µL HGH antibody-dye conjugate solution (Example 2) to each vial. Incubation was continued for an addition hour at 37° C. after which SERS spectra were collected for each vial.

Example 6d

Human Growth Hormone (HGH) Immunoassay in Teflon Coated Microwell Plate: In separate 300 µL teflon coated microwells placed 50 µL HGH antibody/1% NaHCO$_3$ (20 µg/mL) and 50 mL silver colloid (Example 1a). The microwell was placed in 37° C. incubator overnight. To each well containing desiccated antibody/silver colloid was added 50 µL HGH antigen/1% NaHCO$_3$. The concentration range of HGH antigen was 0 ng/mL to 40 ng/mL. The microwell plate containing antibody/colloid-antigen was incubated at 37° C. for 1 hr, followed by addition of 50 µL HGH antibody-dye conjugate solution (Example 2) to each well. Incubation was continued for an addition hour at 37° C. after which SERS spectra were collected for each well.

Example 7

Polychlorinated Biphenyl (PCB) Immunoassay in Parafilm Coated Microwell Plate: In separate 100 µL Parafilm coated microwells placed 50 µL PCB antibody/1% NaHCO$_3$ (25 µg/mL) and 50 µL silver colloid (Example 1a). The microwell was placed in 37° C. incubator overnight. To each well containing desiccated antibody/silver colloid was added 50 µL of an aqueous solution of PCB analyte. The aqueous solutions of PCB analyte were prepared by first dissolving 10 µg Aroclor 1248 in 1 mL hexane followed by appropriate dilutions using millipore water and evaporation of the hexane. The concentration range of PCB analyte was 0 ng/mL (ppb) to 50 ng/mL (ppb). The microwell plate containing antibody/colloid-analyte was incubated at 37° C. for 30 min, followed by addition of 50 L PCB antibody-dye conjugate solution (Example 3) to each well. Incubation was continued for an additional 30 min at 37° C. after which SERS spectra were collected for each well.

Example 8

Polychlorinated Biphenyl (PCB) Immunoassay in Parafilm Coated Microwell Plate: In separate 100 pL Parafilm coated microwells placed 50 µL PCB antibody/1% NaHCO$_3$ (25 µg/mL) and 50 µL silver colloid (Example 1a). The microwell was placed in 37° C. incubator overnight. To each well containing desiccated antibody/silver colloid was added 50 µL of an aqueous solution of PCB analyte. The aqueous solutions of PCB analyte were prepared by first dissolving 10 µg Aroclor 1248 in 1 mL hexane followed by appropriate dilutions using millipore water and evaporation of the hexane. The concentration range of PCB analyte was 0 ng/mL (ppb) to 50 ng/mL (ppb). The microwell plate containing antibody/colloid-analyte was incubated at 37° C. for 30 min, followed by addition of 50 µL BSA-reactive blue dye conjugate solution (Example 4b) to each well. Incubation was continued for an additional 30 min at 37° C. after which SERS spectra were collected for each well.

Example 9

Polychlorinated Biphenyl (PCB) Immunoassay in Parafilm Coated Microwell Plate: In separate 100 µL Parafilm coated microwells placed 50 µL PCB antibody/1% NaHCO$_3$ (25 µg/mL) and 50 µL silver colloid (Example 1a). The microwell was placed in 37° C. incubator overnight. To each well containing desiccated antibody/silver colloid was added 50 μL of an aqueous solution of PCB analyte. The aqueous solutions of PCB analyte were prepared by first dissolving 10 μg Aroclor 1248 in 1 mL hexane followed by appropriate dilutions using millipore water and evaporation of the hexane. The concentration range of PCB analyte was 0 ng/mL (ppb) to 50 ng/mL (ppb). The microwell plate containing antibody/colloid-analyte was incubated at 37° C. for 30 min, followed by addition of 50 μL anti-mouse IgG-FITC conjugate solution (Example 5) to each well. Incubation was continued for an additional 30 min at 37° C. after which SERS spectra were collected for each well.

Example 10

Polychlorinated Biphenyl (PCB) Extraction from Soil Immunoassay in Parafilm Coated Microwell Plate: Standard solutions of Aroclor 1248 (PCB) were prepared by dissolving the PCB in hexane. To each standard PCB solution was added a known weight of oven-dried soil. The soil/PCB samples were stirred vigorously for 30 min followed by evaporation of the hexane solvent. To each dried soil sample was added 2 mL hexane and 2 mL millipore water. The samples were stirred for 30 min then centrifuged and the hexane transferred to clean vials. This extraction was repeated a second time combining the hexane transfers. To each hexane vial was added 1 mL of a 1 M $FeCl_3$ which had been adjusted to pH 6 with $NaHCO_3$, then shaken vigorously for 1 min followed by centrifugation. The hexane layer was transferred to clean vials then evaporated. The PCB residue was re-dissolved in 1 mL of a 1:1 millipore water/methanol solution. In separate 100 μL Parafilm coated microwells was placed 50 μL PCB antibody/1% $NaHCO_3$ (25 μg/mL) and 50 μL silver colloid (Example 1a). The microwell was placed in 37° C. incubator overnight. To each well containing desiccated antibody/silver colloid was added 50 μL of a water/methanol solution of PCB soil extracted analyte. The concentration range of PCB analyte was 100 μg/mL (pptr) to 20 ng/mL (ppb). The microwell plate containing antibody/colloid-analyte was incubated at 37° C. for 30 min, followed by addition of 50 μL BSA-reactive blue dye conjugate solution (Example 4b) to each well. Incubation was continued for an additional 30 min at 37° C. after which SERS spectra were collected for each well.

Example 11

Polychlorinated Biphenyl (PCB) One-Step Analyte Addition Immunoassay in Parafilm Coated Microwell Plate: In separate 100 μL Parafilm coated microwells was placed 50 μL PCB antibody/1% $NaHCO_3$ (25 μg/mL) and 50 μL silver colloid (Example 1a). The microwell plate was placed in 37° C. incubator overnight. To each well containing desiccated antibody/silver colloid was added 50 μL BSA-reactive blue dye conjugate solution (Example 4b). The microwell plate was placed in 37° C. incubator for 1-2 hr to desiccate antibody/silver colloid/BSA-dye conjugate. Aqueous solutions of PCB analyte were prepared by first dissolving 10 μg Aroclor 1248 in 1 mL hexane followed by appropriate dilutions using millipore water and evaporation of the hexane. The concentration range of PCB analyte was 1 ng/mL (ppb) to 12.5 ng/mL (ppb) added to the individual microwells in 50 μL aliquots. The microwell plate containing the re-dispersed antibody/colloid with BSA-reactive blue dye conjugate and analyte was incubated at 37° C. for 30 min after which SERS spectra were collected for each well.

Example 12

Polychlorinated Biphenyl (PCB) One-Step Analyte Addition Immunoassay in Fluorinated Grease Coated Microwell Plate: In separate 100 mL fluorinated grease coated microwells placed 50 μL PCB antibody/1% $NaHCO_3$ (25 mg/mL) and 50 μL silver colloid (Example 1a). The microwell plate was placed in 37° C. incubator overnight. To each well containing desiccated antibody/silver colloid was added 50 μL BSA-reactive blue dye conjugate solution (Example 4b). The microwell plate was placed in 37° C. incubator for 1–2 hr to desiccate antibody/silver colloid/BSA-dye conjugate. Aqueous solutions of PCB analyte were prepared by first dissolving 10 μg Aroclor 1248 in 1 mL hexane followed by appropriate dilutions using millipore water and evaporation of the hexane. The concentration range of PCB analyte was 1 ng/mL (ppb) to 12.5 ng/mL (ppb) added to the individual microwells in 50 μL aliquots. The microwell plate containing the re-dispersed antibody/colloid with BSA-reactive blue dye conjugate and analyte was incubated at 37° C. for 30 min after which SERS spectra were collected for each well.

Example 13

Polychlorinated Biphenyl (PCB) One-Step Immunoassay in Pretreated Low Affinity Micro-miniwell Plate: In separate 10 μL pretreated low affinity micro-miniwells placed 5 μL PCB antibody/1% $NaHCO_3$ (25 mg/mL) and 5 μL silver colloid (Example 1a). The microwell plate was placed in 37° C. incubator for 1 hr. To each well containing desiccated antibody/silver colloid was added 5 μL BSA-reactive blue dye conjugate solution (Example 4b). The microwell plate was placed in 37° C. incubator for 1 hr to desiccate antibody/silver colloid/BSA-dye conjugate. Aqueous solutions of PCB analyte were prepared by first dissolving 10 μg Aroclor 1248 in 1 mL hexane followed by appropriate dilutions using millipore water and evaporation of the hexane. The concentration range of PCB analyte was 1 ng/mL (ppb) to 12.5 ng/mL (ppb) added to the individual microwells in 10 μL aliquots. The microwell plate containing the re-dispersed antibody/colloid with BSA-reactive blue dye conjugate and analyte was incubated at 37° C. for 30 min after which SERS spectra were collected for each well.

Example 14

Detection of Bilirubin using a Reactive Coating on Silver Foil: Prepared silver foil (Example 1d) was pre-coated with a self-assembled monolayer (SAM) of octanethiol (C8) by dip-coating the silver foil surface in a 1 mM ethanol solution of octanethiol followed by an ethanol rinse. A tetrahydrofuran (THF) solution of a diazonium coating was then applied to the C8 coated foil. After evaporation of the THF the diazonium coating is physisorbed to the C8 coating, bound by a hydrophobic reaction. An ethanol solution of bilirubin was then applied to the C8-diazonium surface. A SERS spectrum of the surface after reaction of the diazonium with bilirubin was collected.

Example 15

Detection and Determination of Bilirubin using a Reactive Coating with a Thiol Tether on Silver Colloids: A 1 mL silver colloid suspension (Example 1b) was mixed with a 100 μL ethanol/bicarbonate solution of bilirubin. The concentration range of the bilirubin solutions was 0 mM to 22 mM. To the mixture of colloid/bilirubin was added 100 μL of an ethanol solution of the diazonium coating. Vials containing the colloid/bilirubin/diazonium mixture were thoroughly mixed for 1 min followed by collection of the SERS spectra.

Example 16

Detection and Quantification of Cyanide using Gold Colloids: To separate vials containing 0.5 mL gold colloid (Example 1c) was added 0.5 mL of an aqueous NaCN solution. The concentration range of cyanide solution was 5 ppb to 250 ppb. The cyanide solution was thoroughly mixed with the colloid suspension followed by collection of SERS spectra.

Example 16b

Detection of Cyanide using Gold Colloids: A 20 mL vial was filled with a gold colloid suspension (Example 1c) and capped securely with a dialysis membrane filter. The vial was placed in 20 mL of a 1 ppm aqueous NaCN solution for 20 min. The colloid vial was removed and a SERS spectrum obtained.

Example 17

Detection of Cyanide using a Reactive Coating on Silver Foil: Prepared silver foil (Example 1d) was pre-coated with a self-assembled monolayer (SAM) of octanethiol (C8) by dip-coating the silver foil surface in a 1 mM ethanol solution of octanethiol followed by an ethanol rinse. A tetrahydrofuran (THF) solution of a diazonium coating was then applied to the C8 coated foil. After evaporation of the THF the diazonium coating is physisorbed to the C8 coating, bound by a hydrophobic reaction. An aqueous solution of NaCN was then applied to the C8-diazonium surface. The concentration range for the NaCN aqueous solutions was 5 ppm to 10,000 ppm. A SERS spectrum of the surface after reaction of the diazonium with cyanide was collected.

Example 18

Detection and Quantification of Amphetamine using a Reactive Coating on Silver Foil: Silver foil was roughened and etched (Example 1d) followed by dip-coating in an $CH_2Cl_2$ solution of MNA/amphetamine containing 3 ppm of a $CH_2Cl_2$ solution of pentachlorothiolphenol (PCTP). The PCTP was used as an internal standard for quantification purposes. The coated foil surfaces were rinsed with ethanol to remove unbound MNA/amphetamine and PCTP. The MNA/amphetamine was synthesized by dissolving 363 mg amphetamine sulfate in 10 mL of an aqueous saturated solution of $K_2CO_3$ to neutralize the sulfate. The freebase drug was then extracted from the aqueous solution using $CH_2Cl_2$ followed by addition of 155 mg 2-mercaptonicotinic acid (MNA) and 206 mg dicyclohexylcarbodiimide (DCC). The reaction was gently refluxed overnight under a nitrogen atmosphere. The MNA/amphetamine reaction product was transferred to a separatory funnel with $CH_2Cl_2$ and washed with an aqueous saturated solution of $NaHCO_3$ to neutralize unreacted MNA, followed by a wash with $H_2O$ and 10% HCl to neutralize unreacted freebase and DCC. Solvent was removed under reduced pressure. The product N-(1-methyl-2-phenylethyl)-2-mercaptopyridine-3-carboxamide (MNA/amphetamine) was re-dissolved in $CH_2Cl_2$ to form standard solutions in the concentration range of 0 ppm to 500 ppm. SERS spectra were obtained from the MNA/amphetamine/PCTP coated silver foil surfaces.

Example 19

Detection and Quantification of Methamphetamine using a Reactive Coating on Silver Foil: Silver foil was roughened and etched (Example 1d) followed by dip-coating in an methanol solution of MNA/methamphetamine containing 2 ppm of a $CH_2Cl_2$ solution of pentachlorothiolphenol (PCTP). The PCTP was used as an internal standard for quantification purposes. The coated foil surfaces were rinsed with ethanol to remove unbound MNA/methamphetamine and PCTP. The MNA/methamphetamine was synthesized by dissolving 186 mg methamphetamine hydrochloride in 15 mL of saturated aqueous $K_2CO_3$ to neutralize the hydrochloride. The freebase was then extracted from the aqueous solution using diethyl ether ($Et_2O$). The ether was removed under reduced pressure and the methamphetamine re-dissolved in 8 mL of ethanol to which was added 169 mg 2-mercaptonicotinic acid (MNA) and 228 mg dicyclohexylcarbodiimide (DCC) in 2mL $H_2O$. The reaction was gently refluxed under a nitrogen atmosphere for 2 hr. The MNA/methamphetamine reaction product was transferred to a separatory funnel using $Et_2O$ and extracted with additional $Et_2O$ followed by washes with saturated aqueous $NaHCO_3$, $H_2O$, and 10% HCl. Solvent was removed under reduced pressure. The product N-methyl-N-(1-methyl-2-phenylethyl)-2-mercaptopyridine-3-carboxamide (MNA/methamphetamine) was re-dissolved in methanol to form standard solutions in the concentration range of 0 ppm to 2500 ppm. SERS spectra were obtained from the MNA/methamphetamine/PCTP coated silver foil surfaces.

Example 20

Detection and Quantification of Morphine using an Active Coating on Silver Foil: Silver foil was roughened and etched (Example 1d) followed by dip-coating in a 200 ppm 0.5 M boric acid solution of 4-(4-(N-ethyl-N-2-thioethyl) aminophenyl) azobenzene-sulfonic acid, sodium salt (azo dye) followed by a rinse with pH 7 phosphate buffer to remove unbound dye. The silver foil was cut to fit diagonally in a 10 mm glass cuvette. Phosphate buffered (pH 7) morphine solutions were added to the cuvette in increasing concentration followed by a routine of decreasing concentration. A SERS spectrum was obtained for each concentration of morphine solution. The concentration range of buffered morphine solution was 0 ppb to 60 ppb.

Example 21

Detection and Quantification of Toluene using a Passive Coating on Silver Colloids: A series of vials were filled with 0.5 mL silver colloid suspension (Example 1a) followed by addition of 10 mL of a 3 ppb ethanol solution of 1-propanethiol to each vial. Standard solutions of toluene dissolved in millipore water were prepared for a concentration range of 0 ppm to 20 ppm. To each vial containing propanethiol coated silver colloid was added 0.5 mL of aqueous toluene solution. A SERS spectrum was collected of each vial.

The discussion included in this patent is intended to serve as a basic description. The reader should be aware that the specific discussion may not explicitly describe all embodiments possible; many alternatives are implicit. It also may not explicitly explain the generic nature of the invention and may not explicitly show how each feature or element can actually be representative of a broader function or of a great variety of alternative or equivalent elements. Again, these are implicitly included in this disclosure. Where the invention is described in process-oriented terminology, each element of the process may be implicitly performed by a device. Process or method claims may not only be included for the process described, but also apparatus claims may be included to address the devices which perform the invention as well as claims directed to the end product produced in these fashions. Neither the description nor the terminology is intended to limit the scope of the claims in this patent.

Further, equivalent, broader, and more generic terms are also implicit in the prior description of each element. Such terms can be substituted when desired to make explicit the implicitly broad coverage to which this invention is entitled. Further, it should be understood that a variety of changes may be made without departing from the essence of the invention. Such changes are also implicitly included in the description. They still fall within the scope of this invention. This disclosure encompasses both the explicit embodiment(s) shown, the great variety of implicit alternative embodiments, and broad methods or processes and the like.

In addition, each of the various elements of the invention and claims may also be achieved in a variety of manners. This disclosure should be understood to encompass each such variation, be it a variation of an embodiment of any apparatus embodiment, a method or process embodiment, or even merely a variation of any element of these. Particularly, it should be understood that as the disclosure relates to elements of the invention, the words for each element may be expressed by equivalent apparatus terms or method terms—even if only the function or result is the same. Such equivalent, broader, or even more generic terms should be considered to be encompassed in the description of each element or action. Such terms can be substituted where desired to make explicit the implicitly broad coverage to which this invention is entitled. As but one example, it should be understood that all actions may be expressed as a means for taking that action or as an element which causes that action. Similarly, each physical element disclosed should be understood to encompass a disclosure of the action which that physical element facilitates. Regarding this last aspect, the disclosure of a "detector" should be understood to encompass disclosure of the act of "detecting"—whether explicitly discussed or not—and, conversely, were there only disclosure of the act of "detecting", such a disclosure should be understood to encompass disclosure of a "detector." Such changes and alternative terms are to be understood to be explicitly included in the description. Further, the applicant should be understood to have support for method and corresponding apparatus claims and for the various combinations and permutations of each element disclosed.

In addition, any references mentioned in the application for this patent as well as all references in the list attached are hereby incorporated by reference in their entirety to the extent such may be deemed essential to support the enablement of the invention or to augment the disclosure. However, to the extent statements in such references might be considered inconsistent with the patenting of this invention, such statements are expressly not to be considered as made by the applicant.

In addition, it should be understood that although claims directed to the methods have been included in various detail, for administrative efficiencies, only initial claims directed toward the apparatus embodiments have been included. Naturally, the disclosure and claiming of the method focus in full detail is to be understood as sufficient to support the full scope of both method and apparatus claims. This includes claims having a system, container, sensor, or other component or facilitating element focus as well. These may be added at a later date when appropriate to explicitly claim such details. Thus, the present disclosure is to be construed as encompassing the full scope of apparatus claims, including but not limited to claims and subclaims similar to those presented in a method context.

What is claimed is:

1. A method of analyte detection, comprising the steps of:
   a. establishing a colloidal substance;
   b. providing said colloidal substance in a liquid;
   c. desiccating said colloidal substance in said liquid to establish a residue of said colloidal substance;
   d. reconstituting said residue of said colloidal substance to generate a colloidal sensor solution containing said colloidal substance;
   e. interacting an analyte with a portion of said colloidal substance contained in said colloidal sensor solution;
   f. subjecting said colloidal sensor solution to an illumination;
   g. affecting said illumination with said portion of said colloidal substance contained in said colloidal sensor solution interacting with said analyte to generate an affected emission; and
   h. spectroscopically analyzing said affected emission to detect said analyte.

2. A method of analyte detection as described in claim 1 wherein said step of establishing a colloidal substance comprises the step of establishing a surface enhanced Raman spectroscopic colloidal substance, and wherein said step of affecting said illumination with said portion of said colloidal substance contained in said colloidal sensor solution interacting with said analyte to generate an affected emission comprises the step of generating a Raman spectral signal, and wherein said step of spectroscopically analyzing said affected emission to detect said analyte comprises the step of analyzing a surface enhanced Raman spectrum.

3. A method of analyte detection as described in claim 2 wherein said step of establishing a surface enhanced Raman spectroscopic substance comprises the step of establishing a surface enhanced Raman spectroscopic substance selected from a group consisting of silver colloids, gold colloids, colloids formed from the chemical reduction of silver salts, colloids formed from the chemical reduction of gold salts, metal colloids, colloids formed from the chemical reduction of metal salts, colloids formed from the electrochemical reduction of metal salts, colloids formed from the electrochemical reduction of gold salts, colloids formed from the electrochemical reduction of silver salts, colloids formed from the ablation of metals, colloids formed from the ablation of silver, and colloids formed from the ablation of gold.

4. A method of analyte detection as described in claim 1 wherein said step of affecting said illumination with said portion of said colloidal substance contained in said colloidal sensor solution interacting with said analyte to generate an affected emission comprises the step of generating a fluorescence spectral signal, and wherein said step of spectroscopically analyzing said affected emission to detect said analyte comprises the step of analyzing said fluorescence spectral signal.

5. A method of analyte detection as described in claim 4 wherein said step of generating a fluorescence spectral signal comprises the step of generating a surface enhanced fluorescence spectral signal.

6. A method of analyte detection as described in claim 1 further comprising the step of coating said colloidal substance with an analyte responsive coating to generate a coated colloidal substance.

7. A method of analyte detection as described in claim 6 wherein said step of coating a portion of said colloidal substance with an analyte responsive coating to generate a coated colloidal substance comprises the step of coating a portion of said colloidal substance with a first analyte responsive coating.

8. A method of analyte detection as described in claim 7 wherein said step of coating a portion of said colloidal substance with an analyte responsive coating to generate a coated colloidal substance comprises the step of coating a second portion of said colloidal substance with a second analyte responsive coating.

9. A method of analyte detection as described in claim 8 wherein said step of reconstituting said residue of said colloidal substance to generate a colloidal sensor solution comprises the step of reconstituting said residue of said coated colloidal substance to generate a colloidal sensor solution containing said coated colloidal substance having said first analyte responsive coating and having said second analyte responsive coating, and wherein said step of interacting an analyte with a portion of said colloidal substance contained in said colloidal sensor solution comprises the step of interacting a first analyte with said first analyte responsive coating.

10. A method of analyte detection as described in claim 9 wherein said step of desiccating said colloidal substance in said liquid to establish a residue of said colloidal substance comprises the step of desiccating said coated colloidal substance having said first analyte responsive coating and said second analyte responsive coating.

11. A method of analyte detection as described in claim 9 wherein said step of interacting an analyte with a portion of said colloidal substance contained in said colloidal sensor solution further comprises the step of interacting a second analyte with said second analyte responsive coating.

12. A method of analyte detection as described in claim 11 wherein said step of interacting a second analyte with said second analyte responsive coating occurs substantially simultaneously with said step of interacting a first analyte with a first analyte responsive coating.

13. A method of analyte detection as described in claim 12 wherein said step of spectroscopically analyzing said affected emission to detect said analyte comprises the step of spectroscopically analyzing said affected emission to detect said first analyte.

14. A method of analyte detection as described in claim 13 wherein said step of spectroscopically analyzing said affected emission to detect said analyte comprises the step of spectroscopically analyzing said affected emission to detect said second analyte.

15. A method of analyte detection as described in claim 6 further comprising the step of selectively interacting an illumination affecting substance with said analyte as said analyte interacts with said portion of said coated colloidal substance contained in said colloidal sensor solution, and wherein said step of affecting said illumination with said portion of said coated colloidal substance contained in said colloidal sensor solution interacting with said analyte to generate an affected emission comprises the step of altering said affected emission by the presence of said illumination affecting substance interacting with said analyte.

16. A method of analyte detection as described in claim 1 further comprising the step of coating said colloidal substance with an analyte-responsive coating to create a coated sensor colloid.

17. A method of analyte detection as described in claim 15 wherein said step of coating said colloidal substance with an analyte responsive coating to generate a coated colloidal substance comprises the step of coating a portion of said colloidal substance with a first analyte responsive coating.

18. A method of analyte detection as described in claim 17 wherein said step of coating said colloidal substance with an analyte responsive coating to generate a coated colloidal substance further comprises the step of coating a second portion of said colloidal substance with a second analyte responsive coating.

19. A method of analyte detection as described in claim 18 wherein said step of interacting an analyte with a portion of said analyte responsive colloidal substance contained in said colloidal sensor solution comprises the step of interacting a first analyte with said first analyte responsive coating, and wherein said step of spectroscopically analyzing said affected emission to detect said analyte comprises the step of spectroscopically analyzing said affected emission to detect said first analyte.

20. A method of analyte detection as described in claim 19 wherein said step of interacting an analyte with a portion of said analyte responsive colloidal substance contained in said colloidal sensor solution comprises the step of interacting a second analyte with said second analyte responsive coating and wherein said step of spectroscopically analyzing said affected emission to detect said analyte comprises the steps of:
  i. spectroscopically analyzing said affected emission to detect said first analyte; and
  ii. spectroscopically analyzing said affected emission to detect said second analyte.

21. A method of analyte detection as described in claim 20 wherein said step of interacting a second analyte with said second analyte reactive coating occurs substantially simultaneously with said step of interacting said first analyte with said first analyte reactive coating.

22. A method of analyte detection as described in claim 21 wherein said step of spectroscopically analyzing said affected emission to detect said first analyte and said step of spectroscopically analyzing said affected emission to detect said second analyte occur substantially simultaneously.

23. A method of analyte detection as described in claim 22 wherein said step of spectroscopically analyzing said affected emission to detect said first analyte and said step of spectroscopically analyzing said affected emission to detect said second analyte comprise the step of analyzing a single spectrum to detect both said first analyte and said second analyte.

24. A method of analyte detection as described in claim 23 wherein said step of coating said colloidal substance with an analyte responsive coating to generate a coated colloidal substance comprises the step of establishing a surface enhanced Raman spectroscopic substance, and wherein said step of affecting said illumination with said portion of said coated colloidal substance contained in said colloidal sensor solution interacting with said analyte to generate an affected emission comprises the step of generating a surface enhanced Raman spectral signal, and wherein said step of spectroscopically analyzing said affected emission to detect said analyte comprises the step of analyzing a surface enhanced Raman spectrum.

25. A method of analyte detection as described in claim 6 wherein said analyte comprises an analyte analog and wherein said step of affecting said illumination with said portion of said coated colloidal substance contained in said colloidal sensor solution interacting with analyte comprises the step of affecting said illumination with said portion of said coated colloidal substance contained in said colloidal sensor solution interacting with said analyte analog.

26. A method of analyte detection as described in claim 6 wherein said step of interacting an analyte with a portion of said coated colloidal substance in said colloidal sensor solution comprises the step of interacting said analyte and interacting an analyte analog with said coated colloidal substance in said sensor colloid solution substantially simultaneously and wherein said step of affecting said illumination with said portion of said coated colloidal substance contained in said colloidal sensor solution interacting with said analyte to generate an affected emission comprises the step of affecting said illumination with said analyte responsive colloidal substance contained in said colloidal sensor solution interacting with said analyte analog and said analyte.

27. A method of analyte detection as described in claim 6 wherein said step of interacting an analyte with a portion of said coated colloidal substance contained in said colloidal sensor solution comprises the step of interacting said analyte with said portion of said coated colloidal substance contained in said sensor colloidal solution prior to interaction of an analyte analog with said coated colloidal substance contained in said sensor colloid solution and wherein said step of affecting said illumination with said portion of said coated colloidal substance contained in said colloidal sensor solution interacting with said analyte to generate an affected emission comprises the step of affecting said illumination with said analyte responsive colloidal substance contained in said colloidal sensor solution interacting with said analyte and said analyte analog.

28. A method of analyte detection as described in claim 6 wherein said step of interacting an analyte with a portion of said coated colloidal substance contained in said sensor colloidal solution comprises the step of interacting said analyte with said portion of said coated colloidal substance contained in said sensor colloidal solution after interaction of said analyte analog with said portion of said coated colloidal substance contained in said sensor colloid solution and wherein said step of affecting said illumination with said portion of said coated colloidal substance contained in said colloidal sensor solution interacting with said analyte to generate an affected emission comprises the step of affecting said illumination with said analyte responsive colloidal substance contained in said colloidal sensor solution interacting with said analyte and said analyte analog.

29. A method of analyte detection as described in claim 26, 27 or 28 wherein said step of interacting an analyte analog with a portion of said coated colloidal substance contained in said colloidal sensor solution generates an intermediate solution, and further comprising the steps of:
  a. subjecting said intermediate solution to an illumination;
  b. affecting said illumination with said portion of said colloidal substance contained in said intermediate solution interacting with said analyte and said analyte analog to generate an intermediate emission; and
  c. spectroscopically analyzing said intermediate emission, and wherein said step of spectroscopically analyzing said affected emission to detect said analyte comprises the step of comparing said affected emission to said intermediate emission.

30. A method of analyte detection as described in claim 6 further comprising the step of interacting an analyte analog with a portion of said coated colloidal substance in said liquid prior to said step of desiccating said coated colloidal substance in said liquid to establish a residue of said colloidal substance.

31. A method of analyte detection as described in claim 30 wherein said step of interacting an analyte with a portion of said coated colloidal substance contained in said colloidal sensor solution generates an intermediate solution, and further comprising the steps of:
  a. subjecting said intermediate solution to an illumination;
  b. affecting said illumination with said analyte interacting with said portion of said coated colloidal substance within said intermediate solution to generate an intermediate emission; and
  c. spectroscopically analyzing said intermediate emission, and wherein said step of spectroscopically analyzing said affected emission to detect said analyte comprises the step of comparing said affected emission to said intermediate emission.

32. A method of analyte detection as described in claim 28 wherein said step of interacting said analyte with said portion of said coated colloidal substance contained in said sensor colloidal solution after interaction of said analyte analog with said portion of said coated colloidal substance contained in said sensor colloid solution comprises the steps of:
  a. binding said analyte analog with said coated colloidal substance contained in said colloidal sensor solution;
  b. displacing said analyte analog from said coated colloidal substance with said analyte; and
  c. replacing said analyte analog with said analyte on said coated colloidal substance.

33. A method of analyte detection as described in claim 25, 26, 27, 28, or 30 wherein said analyte analog comprises a tagged analyte analog.

34. A method of analyte detection as described in claim 33 wherein said step of binding a tagged analyte analog with at least some of said sensor colloid complex comprises the step of binding a tagged analyte with at least some of said sensor colloid complex.

35. A method of analyte detection as described in claim 28 wherein said step of spectroscopically analyzing said affected emission to detect said analyte comprises the step of analyzing to observe a decrease in said affected emission.

36. A method of analyte detection as described in claim 6 wherein said step of coating a portion of said colloidal substance with an analyte responsive coating to generate an coated colloidal substance comprises the steps of:
  i. coating a first portion of said colloidal substance with a first analyte responsive substance to generate a first coated colloidal substance having a first analyte responsive coating, and
  ii. coating a second portion of said colloidal substance with a second analyte responsive substance to generate a second coated colloidal substance having a second analyte responsive coating, wherein said step of reconstituting said residue of said coated colloidal substance to generate a colloidal sensor solution containing said coated colloidal substance comprises the step of reconstituting a residue mixture of said first coated colloidal substance having said first analyte responsive coating and said second coated colloidal substance having said second analyte responsive coating to generate a colloidal sensor solution containing said first coated colloidal substance and said second coated colloidal substance, and wherein said step of interacting an analyte with a portion of said analyte responsive colloidal substance contained in said colloidal sensor solution comprises the step of interacting a first analyte with said first coated colloidal substance contained in said colloidal sensor solution.

37. A method of analyte detection as described in claim 36 and further comprising the step of mixing said first sensor colloid complex and said second sensor colloid complex together.

38. A method of analyte detection as described in claim 36 and wherein said step of interacting an analyte with a portion of said coated colloidal substance contained in said colloidal sensor solution further comprises the step of interacting a second analyte with said second coated colloidal substance contained in said colloidal sensor solution, and wherein said step of spectroscopically analyzing said affected emission to detect said analyte comprises the steps of:
  i. spectroscopically analyzing said affected emission to detect said first analyte; and
  ii. spectroscopically analyzing said affected emission to detect said second analyte.

39. A method of analyte detection as described in claim 38 wherein said step of interacting a second analyte with said second coated colloidal substance contained in said colloidal sensor solution occurs substantially simultaneously with said step of interacting a first analyte with said first coated colloidal substance contained in said colloidal sensor solution.

40. A method of analyte detection as described in claim 39 wherein said step of spectroscopically analyzing said affected emission to detect said first analyte and said step of spectroscopically analyzing said affected emission to detect said second analyte occur substantially simultaneously.

41. A method of analyte detection as described in claim 40 wherein said step of spectroscopically analyzing said affected emission to detect said first analyte and said step of spectroscopically analyzing said affected emission to detect said second analyte comprise the step of analyzing a single spectra to detect both said first analyte and said second analyte.

42. A method of analyte detection as described in claim 41 wherein said step of establishing a coated colloidal substance responsive to at least one analyte comprises the step of establishing a surface enhanced Raman spectroscopic substance, wherein said step of affecting said illumination with said portion of said coated colloidal substance contained in said sensor colloidal solution interacting with said analyte comprises the step of producing a Raman spectral signal, and wherein said step of spectroscopically analyzing said affected emission to detect said analyte comprises the step of analyzing a surface enhanced Raman spectrum.

43. A method of analyte detection as described in claim 6 further comprising the step of providing a spectroscopic marker retained by said coated colloidal substance.

44. A method of analyte detection as described in claim 6 further comprising the step of providing a spectroscopic marker retained by said analyte.

45. A method of analyte detection as described in claim 6 further comprising the step of providing a spectroscopic marker retained by said analyte analog.

46. A method of analyte detection as described in claim 43 wherein said step of providing a spectroscopic marker retained by said coated colloidal substance further comprises the step of introducing said spectroscopic marker during said step of reconstituting said residue of said coated colloidal substance to generate a colloidal sensor solution.

47. A method of analyte detection as described in claim 43, 44, 45, or 46 wherein said spectroscopic marker comprises a dye.

48. A method of analyte detection as described in claim 47 wherein said step of providing a spectroscopic marker retained by said analyte comprises the steps of:
  i. providing a first dye retained by a first analyte; and
  ii. providing a second dye retained by a second analyte, and wherein said first dye and said second dye affect said illumination differently.

49. A method of analyte detection as described in claim 1 or 6 further comprising the step of including a reconstitution substance with said colloidal substance when desiccating said colloidal substance to establish a residue of said colloidal substance.

50. A method of analyte detection as described in claim 6 further comprising the step of including a reconstitution substance with said colloidal substance when desiccating said colloidal substance to establish a residue of said colloidal substance.

51. A method of analyte detection as described in claim 49 further comprising the step of coordinating a container with said colloidal substance prior to desiccation to permit reconstitution of said residue of said analyte responsive colloidal substance in said container.

52. A method of analyte detection as described in claim 50 further comprising the step of coordinating a container with said coated colloidal substance prior to desiccation to permit reconstitution of said residue of said analyte responsive colloidal substance in said container.

53. A method of analyte detection as described in claim 15 wherein said step of selectively interacting an illumination affecting substance with said analyte as said analyte interacts with said coated colloidal substance contained in said colloidal sensor solution comprises binding a reagent to said analyte while said analyte interacts with said coated colloidal substance contained in said colloidal sensor solution.

54. A method of analyte detection as described in claim 6 wherein said step of coating said colloidal substance with an analyte responsive coating to generate an coated colloidal substance comprises a step selected from the group consisting of binding an antibody to said colloidal substance, binding polyclonal antibodies to said colloidal substance, binding monoclonal antibodies to said colloidal substance, binding polyclonal antibodies to a first antigen and binding polyclonal antibodies to a second antigen to said colloidal substance, binding monoclonal antibodies to a first antigen and binding polyclonal antibodies to a second antigent to said colloidal substance, and binding at least one reagent to said colloidal substance.

55. A method of analyte detection as described in claim 54 wherein said step of coating said colloidal substance with an analyte responsive coating to generate an coated colloidal substance comprises the steps of:

i. coating a portion of said colloidal substance with a first analyte responsive coating to a first analyte responsive colloidal substance having a first analyte responsive coating, and ii. coating another portion of said colloidal substance with a second analyte responsive coating to generate a second analyte responsive colloidal substance having a second analyte responsive coating, and wherein said step of reconstituting said residue of said coated colloidal substance to generate a colloidal sensor solution containing said coated colloidal substance comprises the step of reconstituting said residue of said coated colloidal substance to generate a colloidal sensor solution containing said first coated colloidal substance and said second coated colloidal substance, and wherein said step of interacting an analyte with said coated colloidal substance contained in said colloidal sensor solution comprises the step of interacting a first analyte with said first analyte responsive colloidal substance contained in said colloidal sensor solution.

56. A method of analyte detection as described in claim 6 wherein said step of coating said colloidal substance with an analyte responsive coating to generate an coated colloidal substance comprises the step of coating said colloidal substance with an analyte responsive coating selected from a group consisting of a virus binding substance, a bacteria binding substance, a fungal spore binding substance, an anthrax binding substance, a coating reactive to heroin, a coating reactive to THC, a coating reactive to morphine, a coating reactive to codeine, a coating reactive to mescaline, a coating reactive to alcohol, a coating reactive to amphetamine, a coating reactive to methamphetamine, a coating reactive to polychlorinated biphenyl (PCB), a coating reactive to phenolic compound, a coating reactive to furan, a coating reactive to pyrrole, a coating reactive to a substance in blood, a coating reactive to a substance in urine, a coating reactive to reactive to bilirubin, a coating reactive to salicylic compound, a coating reactive to neurotransmitter, a coating reactive to human growth hormone, a coating reactive to thyroid stimulating hormone, antibodies to a hormone, antibodies to a protein, antibodies to a bacteria, antibodies to a virus, antibodies to a prion, antibodies to human growth hormone, antibodies to thyroid stimulating hormone, antibodies to prostate specific antigen, antibodies to h. Pylori, antibodies to giardia, antibodies to a prion protein, antibodies to trinitrotoluene, and antibodies to polychlorinated biphenyls.

57. A method of analyte detection as described in claim 15 wherein said step of selectively interacting an illumination affecting substance with said analyte as said analyte interacts with said coated colloidal substance contained in said colloidal sensor solution comprises the step of selectively interacting an illumination affecting substance selected from the group consisting of a spectroscopically marked antibody, spectroscopically marked polyclonal antibodies, spectroscopically marked monoclonal antibodies, spectroscopically marked antibodies to a hormone, spectroscopically marked antibodies to a protein, spectroscopically marked antibodies to a bacteria, spectroscopically marked antibodies to a virus, spectroscopically marked antibodies to a prion, spectroscopically marked antibodies to human growth hormone, spectroscopically marked antibodies to thyroid stimulating hormone, spectroscopically marked antibodies to prostate specific antigen, spectroscopically marked antibodies to h. Pylori, spectroscopically marked antibodies to giardia, spectroscopically marked antibodies to a prion protein, spectroscopically marked antibodies to trinitrotoluene, and spectroscopically marked antibodies to polychlorinated biphenyls.

58. A method of analyte detection as described in claim 26, 27, 28, or 30 wherein said analyte analog is selected from a group consisting of a morphine analog, a morphine analog with a phthalocyanine dye, a methamphetamine analog, amphetamine analog with an azo dye, tetrahydrocannibinol analog, tetrahydrocannibinol with an aminotriarylmethane dye, a 2,4-dichlorophenoxyacetic acid analog, a 2,4-dichlorophenoxyacetic acid analog with an azo dye, a carbofuran analog, and a carbofuran analog with an aminotriarylmethane dye.

59. A method of analyte detection as described in claim 43 wherein said step of providing a spectroscopic marker retained by said coated colloidal substance comprises the step of providing a spectroscopic marker selected from the group consisting of a SERS marker, a phthalocyanine, a aminotriarylmethane, an oxazine, an anthraquinone, a xanthene, an indigoid, a carbocyanine, an azine, a thiazine, a coumarin, and an azo dye.

60. A method of analyte detection as described in claim 49 wherein said step of including a reconstitution substance with said colloidal substance when desiccating said colloidal substance to establish a residue of said colloidal substance comprises the step of including a reconstitution substance selected from the group consisting of a hydrocarbon, a paraffin, an organosilicon material, an oxygenated derivative of an organosilicon material, a fluorocarbon, a teflon material, a polyether, an oxygenated analog of a hydrocarbon, a perfluorocarbon, a hydrophobic substance, a halogenated hydrocarbon, an agent having a similar charge to that on the analyte responsive colloidal substance, a polyether, polyethylene glycol, a salt of inorganic derivatives of sulphuric acid, a salt of organic derivatives of sulphuric acid, a sulphonic acid, a phosphoric acid, a phosphonic acid, a carboxylic acid, a substance containing a free acid of a sulphate monoester, a substance containing a free acid of a sulfonic acid, a substance containing a free acid of a phosophate monoester, a substance containing a free acid of a phosophate diester, a substance containing a free acid of a phosphonic acid, a substance containing a free acid of a phosophate monoester, a substance containing a free acid of a carboxylic acid, a substance containing a salt of a sulphate monoester, a substance containing a salt of a sulfonic acid, a substance containing a salt of a phosophate monoester, a substance containing a salt of a phosophate diester, a substance containing a salt of a phosphonic acid, a substance containing a salt of a phosophate monoester, and a substance containing a salt of a carboxylic acid.

61. A method of analyte detection as described in claim 50 wherein said step of including a reconstitution substance with said coated colloidal substance when desiccating said colloidal substance to establish a residue of said coated colloidal substance comprises the step of including a reconstitution substance selected from the group consisting of a hydrocarbon, a paraffin, an organosilicon material, an oxygenated derivative of an organosilicon material, a fluorocarbon, a teflon material, a polyether, an oxygenated analog of a hydrocarbon, a perfluorocarbon, a hydrophobic substance, a halogenated hydrocarbon, an agent having a similar charge to that on the analyte responsive colloidal substance, a polyether, polyethylene glycol, a salt of inorganic derivatives of sulphuric acid, a salt of organic derivatives of sulphuric acid, a sulphonic acid, a phosphoric acid, a phosphonic acid, a carboxylic acid, a substance containing a free acid of a sulphate monoester, a substance containing a free acid of a sulfonic acid, a substance containing a free acid of a phosophate monoester, a substance containing a free acid of a phosophate diester, a substance containing a free acid of a phosphonic acid, a substance containing a free acid of a phosophate monoester, a substance containing a free acid of a carboxylic acid, a substance containing a salt of a sulphate monoester, a substance containing a salt of a sulfonic acid, a substance containing a salt of a phosophate monoester, a substance containing a salt of a phosophate diester, a substance containing a salt of a phosphonic acid, a substance containing a salt of a phosophate monoester, and a substance containing a salt of a carboxylic acid.

62. A method of analyte detection as described in claim 14 wherein said step of spectroscopically analyzing said affected emission to detect said analyte comprises the step of spectroscopically analyzing said affected emission to detect said first analyte and to detect said second analyte simultaneously from a single spectrum.

63. A method of analyte detection as described in claim 44 further comprising the step of displacing said spectroscopic marker retained by said analyte.

64. A method of analyte detection as described in claim 45, further comprising the step of displacing said spectroscopic marker retained by said analyte analog.

65. A method of analyte detection as described in claim 63, wherein said step of displacing said spectroscopic marker retained by said analyte responsive colloidal substance decreases said affected emission.

66. A method of analyte detection as described in claim 64, wherein said step of displacing said spectroscopic marker retained by said analyte decreases said affected illumination.

* * * * *